United States Patent [19]
Schlessinger et al.

[11] Patent Number: 5,837,524
[45] Date of Patent: Nov. 17, 1998

[54] PYK2 RELATED POLYNUCLEOTIDE PRODUCTS

[75] Inventors: Joseph Schlessinger, New York, N.Y.; Sima Lev, San Carlos, Calif.

[73] Assignees: Sugen, Inc., Redwood City, Calif.; New York University, New York, N.Y.

[21] Appl. No.: 357,642

[22] Filed: Dec. 15, 1994

[51] Int. Cl.$^6$ .............................. C12N 15/64; C12N 1/21; C07H 21/04

[52] U.S. Cl. ................................... 435/252.3; 435/320.1; 435/91.4; 536/23.1; 536/25.4

[58] Field of Search .................................. 536/23.1, 25.4; 435/252.3, 320.1, 91.4

[56] References Cited

U.S. PATENT DOCUMENTS

| | | |
|---|---|---|
| 3,691,016 | 9/1972 | Patel . |
| 3,969,287 | 7/1976 | Jaworek et al. . |
| 4,195,128 | 3/1980 | Hildebrand et al. . |
| 4,215,051 | 7/1980 | Schroeder et al. . |
| 4,229,537 | 10/1980 | Hodgins et al. . |
| 4,247,642 | 1/1981 | Hirohara et al. . |
| 4,330,440 | 5/1982 | Ayers et al. . |
| 4,343,940 | 8/1982 | Kreighbaum et al. . |
| 4,376,110 | 3/1983 | David et al. . |
| 4,447,608 | 5/1984 | Jones et al. . |
| 4,757,072 | 7/1988 | Kabbe et al. . |
| 4,946,778 | 8/1990 | Ladner et al. . |
| 5,316,553 | 5/1994 | Kaul et al. . |

FOREIGN PATENT DOCUMENTS

| | | |
|---|---|---|
| 0520722 | 6/1992 | European Pat. Off. . |
| 0562734 | 3/1993 | European Pat. Off. . |
| 9323569 | 11/1993 | WIPO . |

OTHER PUBLICATIONS

Whitney et al (DNA Cell Biol, 1993, 12:823–830).

Aaronson, S., "Growth Factors and Cancer," *Science* 254:1146–1153 (1991).

Adelman et al., "In Vitro Deletional Mutagenesis for Bacterial Production of the 20,000–Dalton Form of Human Pituitary Growth Hormone," *DNA* 2(3):183–193 (1983).

Allen et al., "Modulation of CD4 by suramin" *Clin. Exp. Immunol.* 91:141–146 (1991).

Anafi et al., "Tyrphostin–Induced Inhibition of p210$^{bcr-abl}$ Tyrosine Kinase Activity Induces K562 to Differentiate," *Blood* 82:3524–3529 (1993).

Baker et al., "Induction of acetylcholine receptor clustering by native polystyrene beads" *Journal of Cell Science* 102:543–555 (1992).

Barker et al., "In vitro activity of non–glutamate containing quinazoline–based thymidylate synthase inhibitors" *Proceedings of the American Association for Cancer Research* 32:327 (#1939) (1991).

Benoist and Chambon, "In vivo sequence requirements of the SV40 early promoter region," *Nature* 290:304–310 (1981).

Bertino, "Toward Improved Selectivity in Cancer Chemotherapy: The Richard and Hinda Rosenthal Foundation Award Lecture" *Cancer Research* 39:293–304 (Feb. 1979).

Bilder et al., "Tyrphostins inhibit PDGF–induced DNA synthesis and associated early events in smooth muscle cells," *Am. J. Physiol.* 206(Cell Physiol.29):C721–C730 (1991).

Bird et al., "Single–Chain Antigen–Binding Proteins," *Science* 242:423–426 (1988).

Bitter et al., "Expression and Secretion Vectors for Yeast," *Methods in Enzym.* 153;516–544 (1987).

Brinster et al., "Factors Affecting the Efficiency of Introducing Foreign DNA into Mice by Microinjecting Eggs," *Proc. Natl. Acad. Sci. USA* 82:4438 (1985).

Brown and Birnbaumer, "Ionic Channels and Their Regulation by G Protein Subunits," *Ann. Rev. Physiol.* 52:197–213 (1990).

Brunton et al., "Anti–tumour activity of novel tryphostins in breast cancer cells." *Proceedings of the American Association for Cancer Research* 33: 558 (1992) (#3335).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Burke, Jr. et al., Bicyclic Compounds as Ring–Constrained Inhibitors of Protein–Tyrosine Kinase p56$^{lck\ 1}$ *Journal of Medicinal Chemistry* 36(4):425–432 (1993).

Burke et al., "Arylamides of Hydroxylated Isoquinolines as Protein–Tyrosine Kinase Inhibitors" *Bioorganic & Medical Chemistry Letters* 2(12):1771–1774 (1992).

Cantrell, D., "G proteins in lymphocyte signalling," *Current in Immunology* 6:380–384 (1994).

Carmeliet, "Ion channel agonists: expectations for therapy," *Eur. Heart J.* 12:30–37 (1991).

Chen and Okayama, "High–Efficiency Transformation of Mammalian Cells by Plasmid DNA," *Mol. and Cell Biol.* 7(8):2745–2752 (1987).

Chowdhury et al., "Long–term Improvement of Hypercholesterolemia After Ex Vivo Gene Therapy in LDLR–Deficient Rabbits," *Science* 254:1082 (1991).

Cobb et al., "Stable Association of pp60$^{src}$ and pp59$^{fyn}$ with the Focal Adhesion–Associated Protein Tyrosine Kinase, pp125$^{FAK}$," *Mol. and Cell. Biol.* 14:147–155 (1994).

Colbère–Garapin et al., "A New Dominent Hybrid Selective Marker for Higher Eukaryotic Cells," *J. Mol. Biol.* 150:1–14 (1981).

(List continued on next page.)

*Primary Examiner*—Lila Feisee
*Assistant Examiner*—Susan Ungar
*Attorney, Agent, or Firm*—Lyon & Lyon LLP

[57] ABSTRACT

The present invention features a method for treatment of an organism having a disease or condition characterized by an abnormality in a signal transduction pathway, wherein the signal transduction pathway includes a PYK2 protein. The invention also features methods for diagnosing such diseases and for screening for agents that will be useful in treating such diseases, The invention also feature purified and/or isolated nucleic acid encoding a PYK2 protein.

25 Claims, 2 Drawing Sheets

OTHER PUBLICATIONS

Cole et al., "The EBV–Hybridoma Technique and its Application to Human Lung Cancer," pp. 77–96 in *Monoclonal Antibodies and Cancer Therapy* eds. Reisfeld and Sell, Alan R. Liss, Inc., New York (1985).

Creighton, T., *Proteins: Structures and Molecular Principles* pp. 79–86, W.H. Freeman and Co., New York, (1983).

Cristiano et al., "Hepatic Gene Therapy: Adenovirus Enhancement of Receptor–Mediated Gene Delivery and Expression in Primary Hepatocytes," *Proc. Natl. Acad. Sci. USA* 90:2122–2126 (1993).

Curiel et al., "Adenovirus Enhancement of Transferrin–Polylysine–Mediated Gene Delivery," *Proc. Nat. Acad. Sci. USA* 88:8850–8854 (1991).

Curtin et al., "Inhibition of the growth of human hepatocellular carcinoma in vitro and in athymic mice by a quinazoline inhibitor of thymidylate synthase, CB3717" *Br. J. Cancer* 53:361–368 (1986).

Dolle et al., "5,7–Dimethoxy–3–(4–pyridinyl)quinoline is a Potent and Selective Inhibitor of Human Vascular β–Type Platelet–Derived Growth Factor Receptor Tyrosine Kinase" *J. Med. Chem.* 37:2627–2629 (1994).

Dolphin, A., "G Protein Modulation of calcium Currents in Neurons," *Ann. Rev. Physiol.* 52:243–55 (1990).

Domchek et al., "Inhibition of SH2 Doamin/Phosphoprotein Association by a Nonhydrolyzable Phosphonopeptide," *Biochemistry* 31:9865–9870 (1992).

Dong et al., "Protein Tyrosine Kinase Inhibitors Decrease Induction of Nitric Oxide Synthase Activity in Lipopolysaccharide–Responsive and Lipopolysaccharide–Nonresponsibe Murine Macrophages" *The Journal of Immunology* 151(5):2717–2724 (Sep. 1993).

Dong et al., "Activation of tumoricidal properties in macrophages by lipopolyasaccharide requires protein–tyrosine kinase activity" *Journal of Leukocyte Biology* 53:53–60 (Jan. 1993).

Fantl et al., "Distinct Phosphotyrosines on a Growth Factor Receptor Bind to Specific Molecules That Mediate Different Signaling Pathways," *Cell* 69:413–423 (1992).

Felder et al., "SH2 Domains Exhibit High–Affinity Binding to Tyrosine–Phosphorylated Peptides Yet Also Exhibit Rapid Dissociation and Exchange," *Mol. and Cell. Biol.* 13(3):1449–1455 (1993).

Felgner and Ringold, "Cationic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413 (1987).

Fernandes et al., "Biochemical and Antitumor Effects of 5,8–Dideazaisopteroylglutamate, a Unique Quinazoline Inhibitor of Thymidylate Synthase" *Cancer Research* 43:1117–1123 (1983).

Ferrari et al., "An in Vivo Model of Somatic Cell Gene Therapy for Human Severl Combined Immunodeficiency," *Science* 251:1363–1366 (1991).

Ferris et al., "Synthesis of Zuinazoline Nucleosides from Ribose and Anthranilonitrile. Application of Phase–Transfer Catalysis in Nucleoside Synthesis," *J. Org. Chem.* 44(2):173–178 (1979).

Fingl and Woodbury, Chapter 1, pp. 1–46 in *The Pharmacologial Basis of Therapeutics* (5th edition), eds., Goodman et al., MacMillan Publishing Co., Inc., New York (1975).

Fischer and Schonbrunn, "Bombesin Receptor is Coupled to a Guanine Nucleotide–binding [Protein?] Which is Insensitive to Pertussis and Cholera Toxins," *J. Biol. Chem.* 263:2808–2816 (1988).

Fischer et al., "Protein Tyrosine Phosphatases: A Diverse Family of Intracellular and Transmembrane Enzymes," *Science* 253:401–406 (1991).

Frucht et al., "Characterization of Functional Receptors for Gastrointestinal Hormones on Human Colon Cancer Cells," *Cancer Research* 52:1114–1122 (1992).

Fry et al., "A Specific Inhibitor of the Epidermal Growth Factor Receptor Tyrosine Kinase" *Science* 465:1093–1095 (Aug. 1994).

Fry et al., "New insights into protein–tyrosine kinase receptor signaling complexes," *Protein Science* 2:1785–1797 (1993).

Gazit et al., "Tyrphostins. 1. Synthesis and Biological Activity of Protein Tyrosine Kinase Inhibitors," *J. Med. Chem.* 32:2344–2352 (1989).

Gazit et al., "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* 34:1896–1907 (1991).

Gazit et al., "Tyrphostins. 3. Structure–Activity Relationship Studies of a α–Substituted Benzylidenemalononitrile 5–S–Aryltyrphostins" *J. Med. Chem.* 36:3556–3564 (1993).

Gehlert and Robertson, "ATP Sensitive Potassium Channels: Potential Drug Targets in Neuropsychopharmacology," *Prog. Neuro–Psychopharmacol. Biol. Psychiatry* 18:1093–1102 (1994).

Gilman, A., "G Proteins: Transducers of Receptor–Generated Signals," *Ann. Rev. Biochem.* 56:615–49 (1987).

Gumbiner, B., "Proteins Associated with the Cytoplasmic Surface of Adhesion Molecules," *Neuron* 11:551–564 (1993).

Hamer and Walling, "Regulation In Vivo of a Cloned Mammalian Gene: Cadmium Induces the Transcription of a Mouse Metallotionein Gene in SV40 Vectors," *J. of Molecular and Applied Genetics* 1:273–288 (1982).

Hildebrand et al., "identification of Sequences Required for the Efficient Localization of the Focal Adhesion Kinase, $pp125^{FAK}$, to Cellular Focal Adhesions," *J. Cell. Biology* 123:993–1005 (1993).

Hille, B., "G Protein–Coupled Mechanisms and Nervous Signaling," *Neuron* 9:187–195 (1992).

Huang et al., "Tyrosine Kinase–Dependent Suppression of a Potassium Channel by the G Protein–Coupled m1 Muscarinic Acetylcholine Receptor," *Cell* 75:1145–1156 (1993).

Huse et al., "Generation of a Large Combinatorial Library of the Immunoglobulin Repertoire in Phage Lambda," *Science* 246:1275–1281 (1989).

Huston et al., "Protein engineering of antibody binding sites: Recovery of specific activity in an anti–digoxin single–chain Fv analogue produced in *Escherichia coli*," *Proc. Natl. Acad. Sci. USA* 85:5879–5883 (1988).

Inouye and Inouye, "Up–promotor mutations in the lpp gene of *Escherichia coli*," *Nucleic Acids Research* 13(9):3100–3111 (1985).

Jackman, "ICI D1694, a Quinazoline Antifolate Thymidylate Synthase Inhibitor That Is a Potent Inhibitor of L1210 Tumor Cell Growth in Vitro and in Vivo: A New Agent for Clinical Study," *Cancer Research* 51:5579–5586 (1991).

Johnston and Hopper, "Isolation of the yeat regulatory gene GAL4 and analysis of its dosage effects on the galactose/melibiose regulon," *Proc. Natl. Acad. Sci. USA* 79:6971–6975 (1982).

Jones, "Quinazoline Antifolates Inhibiting Thymidylate Synthase: Varation of the Amino acid," *J. Med. Chem.* 29:1114–1118 (1986).

Kaur, "Tyrphostin induced growth inhibition: correlation with effect on $p210^{bcr-abl}$ autokinase activity in K562 chronic myelogenous leukemia," *Anti–Cancer Drugs* 5;213–222 (1994).

King, "Site–specific dephosphorylation and deactivation of the human insulin receptor tyrosine kinase by particular and soluble phosphotyrosyl protein phosphatases," *Biochem. Journal* 725:413–418 (1991).

Köhler and Milstein, "Continuous cultures of fused cells secreting antibody of predefined specificity," *Nature* 256:495–496 (1975).

Kozbor and Roder, "The production of monoclonal antibodies from human lymphocytes," *Immun. Today* 4(3):72–79 (1983).

Kuo, "Effects of signalling transduction modulators on the transformed phenotypes in v–H–ras–transformed NIH 3T3 cells," *Cancer Letters* 74:197–202 (1993).

Lam et al., "A new type of synthetic peptide library for identifying ligand–binding activity," *Nature* 354:82–84 (1991).

Lemus, "Studies of Extended Quinone Methides, Synthesis, and Physical Studies of Purine–like Monofunctional Imidazo[4,5–g]quinazoline Reductive Alkylating Agents," *J. Org. Chem.* 54:3611–3618 (1989).

Levitzki, "Tyrphostins: tyrosine kinase blockers as novel antiproliferative agents and dissectors of signal transduction," *FASEB Journal* 6:3275–3282 (1992).

Ley and Seng, "Synthesen unter Verwendung von Benzofuroxan," *Synthesis* 1975:415–422 (1975).

Logan and Shenk, "Adenovirus tripartite leader sequence enhances translation of mRNAs late after infection," *Proc. Natl. Acad. Sci. USA* 81:3655–3659 (1984).

Lowy et al., "Isolation of Transforming DNA: Cloning the Hamster apart Gene," *Cell* 22:817–823 (1980).

Lyall et al., "Tyrphostins Inhibit Epidermal Growth Factor (EGF)–Receptor Tyrosine Kinase Activity in Living Cells and EGF–stimulated Cell Proliferation," *J. Bio. Chem.* 264:14503–14509 (1989).

Maguire, "A new series of PDGF Receptor Tyrosine Kinase Inhibitors: 3–Sustituted Quinoline Derivatives," *J. Med. Chem.* 37:2129–2137 (1994).

Manser et al. "A non–receptor tyrosine kinase that inhibits the GTPase activity of $p21^{cdc42}$," *Nature* 363:364–367 (1993).

Marasco et al., "Design, intracellular expression, and activity of a human anti–human immunodeficiency virus type 1 gp120 single–chain antibody," *Proc. Natl. Acad. Sci. USA* 90:7889–7893 (1993).

Maxwell, "$^{19}$F Nuclear Magnetic Resonance Imaging of Drug Distribution in Vivo: The Siposition of an Antifolate Anticancer Frug in Mice," *Magnetic Resonance in Medicine* 17:189–196 (1991).

McKnight, S.L., "Functional Relationships between Transcriptional Control Signals of the Thymidine Kinase Gene of Herpes Simplex Virus," *Cell* 31:355–365 (1982).

Millauer et al., "Glioblastoma growth inhibited in vivo by a dominant–negative Flk–1 mutant," *Nature* 367:576–579 (1994).

Miller and Rosman, "Improved Retroviral Vectors for Gene Transfer and Expression," *Biotechniques* 7(9):982–988 (1989).

Miller, A.D., "Human gene therapy comes of age," *Nature* 357:455–460 (1992).

Mini, "Cytotoxic Effects of Folate Antagonists against Methotrexate–resistant Human Leukemic Lymphoblast CCRF–CEM Cell Lines," *Cancer Research* 45:325–330 (1985).

Morrison et al., "Chimeric human antibodymolecules: Mouse antigen–binding domains with human constant region domains," *Proc. Natl. Acad. Sci. USA* 81:6851–6855 (1984).

Mulligan and Berg, "Selection for animal cells that express the *Escherichia coli* gene coding for xanthine–guanine phosphoribosyltransferase," *PNAS* 78(4):2072–2076 (1981).

Mulligan, "The Basic Science of Gene Therapy," *Science* 260:926–932 (1993).

Murphy et al., "ATP–sensitive potassium channels counteract anoxia in neurons of the substantia niagra," *Exp. Brain Res.* 84:355–358 (1991).

Nelson, "Detection of Acridinium Esters by the Chemiluminescence," *Nonisotopic DNA Probe Techniques*, ed. Larry J. Kricka, (San Diego: Academic Press, Inc.) pp. 275–310 (1992).

Neuberger et al., "Recombinant antibodies possessing novel effector functions," *Nature* 312:604–608 (1984).

O'Hare et al., "Transformation of mouse fibroblasts to methotrexate resistance by a recombinant plasmid expressing a prokaryotic dihydrfolate reductase," *PNAS* 78(3):1527–1531 (1981).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Phillips, "Quino[1,2–c]quinzalines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chemistry* 17:1489–1496 (1980).

Pillemer, "Insulin Dependence of Murine Lymphoid T–Cell Leukemia," *J. Cancer* 50:80–85 (1992).

Posner, "Kinetics of Inhibition by Tyrphostins of the Tyrosine Kinase Activity of the Epidermal Growth Factor Receptor and Analysis by a New Computer Program," *Molecular Pharmacology* 45:673–683 (1993).

Reece, "Pharmacokinetics of Trimetrexate Administered by Five–Day Continuous Infusion to Patients with Advanced Cancer," *Cancer Research* 47:2996–2999 (1987).

Rendu et al., "Inhibition of Platelet Activation by Tyrosine Kinase Inhibitors," *Biochem. Pharm.* 44(5):881–888 (1992).

Ridley and Hall, "The Small GTP–Binding Protein rho Regulates the Assembly of Focal Adhesions and Actin Stress Fibers in Response to Growth Factors," *Cell* 70:389–399 (1992).

Rodriguez–Pena et al., "Rapid Dephosphorylation of a Mr 80000 Protein, a Specific Substrate of Protein Kinase C Upon removal of Phorbol Esters, Bomesin and Vasopressin," *Biochemical and Biophysical Communications* 140:379–385 (1986).

Rotin et al., "SH2 domains prevent tyrosin dephosphorylation of the EGF receptor: identification of Tyr992 as the high–affinity binding site for SH2 domains of phospholipase Cγ," *The EMBO J.* 11(2):559–567 (1992).

Santerre et al., "Expression of prokaryotic genes for hygromycin B and G418 resistance as dominant–selection markers in mouse L cells," *Gene* 30:147–156 (1984).

Sauro, "Decreased Sensitivity of Aorta from Hypertensive Rats to Vasorelazation by Tyrphostin," *Life Sciences* 53:371–376 (1993).

Sauro, "Tyrphostin Attenates Platelet–Derived Growth Factor–Induced Contraction in Aortic Smooth Muscle Through Inhibition of Protein Tyrosine Kinase(s)," *The Journal of Pharamacology and Experimental Therapeutics* 267:1119–1125 (1993).

Schaller et al., "pp125$^{FAK}$, a structurally distinctive protein–tyrosine kinase associated with focal adhesions," *Proc. Natl. Acad. Sci. USA* 89:5192–5196 (1992).

Schaller et al., "Autonomous Expression of a Noncatalytic Domain of the Focal Adhesion–Associated Protein Tyrosine Kinase pp125$^{FAK}$," *Mol. and Cell. Biol.* 13;785–791 (1993).

Schaller and Parsons, "Focal adhesion kinase: an integrin-–linked protein tyrosine kinase".

Schlessinger, J., "Signal transduction by allosteric receptor oligomerization," *Trends Biochem. Sci.* 13:443–447 (1988).

Schrey et al., "Bombesin and Glucocorticoids Stimulate Human Breast Cancer Cells to Produce Endohelin, a Paracrine Mitogen for Breast Stromal Cells," *Cancer Research* 52:1786–1790 (1992).

Sculier, "Role of an Intensive Care Unit (ICU) In a Medical Onocology Department," *Cancer Immunol. and Immunotherapy* 23;65 (1986).

Shattil et al., "Tyrosine Phosphorylation of pp125$^{FAK}$ in Platelets Requires Coordinated Signalling through Integrin and Agonist Receptors," *J. Biol. Chem.* 269:14738–14745 (1994).

Sikora, "Quinazoline CB 3717 and CB 3703 Inhibitors of Folate Retention and Metabolism in Enrlich Ascites Carcinoma Cells and Some Organs of teh Host–Mouse," *Cancer Letters* 23:289–295 (1984).

Sikora, "Development of an Assay for the Estimation of N$^{10}$–Propargyl–5,8–dideazafolic Acid Polyglutamates in Tumor Cells," *Analytical Biochemistry* 172:344–355 (1988).

Silver et al., "Amino terminus of the yeast GAL4 gene product is sufficient for nuclear localization," *Proc. Natl. Acad. Sci. USA* 81:5951–5955 (1984).

Simon and Lin, "Potassium Channel Openers Block Seizure Activity In an In–Vitro MOdel of Epilepsy," *Biophys. J.* 64:A100 (1993).

Skolnik et al., "Cloning of PI3 Kinase–Associated p85 Utilizing a Novel Method for Expression/Cloning of Target Proteins for Receptor Tyrosin Kinases," *Cell* 65:83–90 (1991).

Songyang et al., "SH2 Domains Recognize Specific Phosphopeptide Sequences," *Cell* 72:767–778 (1993).

Szybalska and Szybalski, "Genetics of Human Cell Lines, IV. DNA–Mediated Heritable Transformation of a Biochemical Trait," *PNAS* 48:20262034 (1962).

Takeda et al., "Construction of chimaeric processed immunoglobulin genes containing mouse variable and human constant region sequences," *Nature* 314:452–454 (1985).

Ullrich and Schlessinger, "Signal Transduction by Receptors with Tyrosine Kinase Activity," *Cell* 61:203–212 (1990).

Van Heeke and Schuster, "Expression of Human Asparagine Synthetase in *Escherichia coli*," *J. Biol. Chem.* 264(10):5503–5509 (1989).

Ward et al., "Binding activities of a repretoire of single immunoglobulin variable domains secreted from *Escherichia coli*," *Nature* 341:544–546 (1989).

Wigler et al., "Transformation of mammalian cells with an amplifiable dominant–acting gene," *Proc. Natl. Acad. Sci. USA* 77(6):3567–3570 (1980).

Wigler et al., "Transfer of Purified Herpes Virus Thymidine Kinase Gene to Cultured Mouse Cells," *Cell* 11:223–232 (1977).

Wilk–Blaszczak et al., "Bradykinin Modulates Potassium and Calcium Currents in Neuroblastoma Hybrid Cells via Different Pertussis Toxin–Insensitive Pathways," *Neuron* 12:109–116 (1994).

Wilson et al., "Distribution and Molecular Characterization of a Cell–Surface and a Cytoplasmic Antigen Detectable in Human Melanoma Cells with Monoclonal Antibodies," *Int. J. Cancer* 28:293–300 (1981).

Wolbring, "Inhibition of GTP–utilizing Enzymes by Tyrphostins," *the Journal of biological Chemistry* 269:22470–22472 (1994).

Wu and Wu, "Receptor–mediated In Vitro Gene Transformation by a Soluble DNA Carrier System," *J. Biol. Chem.* 262:4429 (1987).

Wu et al., "Receptor–Mediated Gene Delivery In Vivo. Partial Correction of Genetic Analbuminemia in Nagas-Rats," *J. Biol. Chem.* 266:14338 (1991) (Abstract).

Wu et al., "Receptor–Mediated Gene Delivery In Vivo," *J. Biol Chem.* 266:14338 (1991).

Yang et al., "Human Very Low Density Lipoprotein Structure: Interaction of the c Apolipoproteins With Apolipoprotein B–100, " *J. Lipid Research* 34:1311 (1993).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

Burgess et al. J. Cell Biol 11:2129–2138, 1990.

Lazar et al. Mol. Cell. Biol. 8:1247–1252, 1988.

Tao et al. J. Immunol. 143(8):2595–2601, 1989.

Gillies et al. Human Antibodies and Hybridoma 1(1):47–54, 1990.

Kawashima, I. 1992. DNA Seq. 2(5): 305–312, 1992.

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
( A ) LENGTH: 1009
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 1:

Met Ser Gly Val Ser Glu Pro Leu Ser Arg Val Lys Leu Gly Thr Leu

```
  1                   5                       10                      15
Arg   Arg   Pro   Glu   Gly   Pro   Ala   Glu   Pro   Met   Val   Val   Val   Pro   Val   Asp
                        20                        25                        30
Val   Glu   Lys   Glu   Asp   Val   Arg   Ile   Leu   Lys   Val   Cys   Phe   Tyr   Ser   Asn
            35                        40                        45
Ser   Phe   Asn   Pro   Gly   Lys   Asn   Phe   Lys   Leu   Val   Lys   Cys   Thr   Val   Gln
            50                        55                        60
Thr   Glu   Ile   Arg   Glu   Ile   Ile   Thr   Ser   Ile   Leu   Leu   Ser   Gly   Arg   Ile
 65                     70                        75                              80
Gly   Pro   Asn   Ile   Arg   Leu   Ala   Glu   Cys   Tyr   Gly   Leu   Arg   Leu   Lys   His
                        85                        90                        95
Met   Lys   Ser   Asp   Glu   Ile   His   Trp   Leu   His   Pro   Gln   Met   Thr   Val   Gly
                        100                       105                       110
Glu   Val   Gln   Asp   Lys   Tyr   Glu   Cys   Leu   His   Val   Glu   Ala   Glu   Trp   Arg
                        115                       120                       125
Tyr   Asp   Leu   Gln   Ile   Arg   Tyr   Leu   Pro   Glu   Asp   Phe   Met   Glu   Ser   Leu
            130                       135                       140
Lys   Glu   Asp   Arg   Thr   Thr   Leu   Leu   Tyr   Phe   Tyr   Gln   Gln   Leu   Arg   Asn
145                           150                       155                             160
Asp   Tyr   Met   Gln   Arg   Tyr   Ala   Ser   Lys   Val   Ser   Glu   Gly   Met   Ala   Leu
                        165                       170                       175
Gln   Leu   Gly   Cys   Leu   Glu   Leu   Arg   Arg   Phe   Phe   Lys   Asp   Met   Pro   His
                        180                       185                       190
Asn   Ala   Leu   Asp   Lys   Lys   Ser   Asn   Phe   Glu   Leu   Leu   Glu   Lys   Glu   Val
                        195                       200                       205
Gly   Leu   Asp   Leu   Phe   Phe   Pro   Lys   Gln   Met   Gln   Glu   Asn   Leu   Lys   Pro
            210                       215                       220
Lys   Gln   Phe   Arg   Lys   Met   Ile   Gln   Gln   Thr   Phe   Gln   Gln   Tyr   Ala   Ser
225                           230                       235                             240
Leu   Arg   Glu   Glu   Glu   Cys   Val   Met   Lys   Phe   Phe   Asn   Thr   Leu   Ala   Gly
                        245                       250                       255
Phe   Ala   Asn   Ile   Asp   Gln   Glu   Thr   Tyr   Arg   Cys   Glu   Leu   Ile   Gln   Gly
                        260                       265                       270
Trp   Asn   Ile   Thr   Val   Asp   Leu   Val   Ile   Gly   Pro   Lys   Gly   Ile   Arg   Gln
            275                       280                       285
Leu   Thr   Ser   Gln   Asp   Ala   Lys   Pro   Thr   Cys   Leu   Ala   Glu   Phe   Lys   Gln
290                           295                       300
Ile   Arg   Ser   Ile   Arg   Cys   Leu   Pro   Leu   Glu   Glu   Gly   Gln   Ala   Val   Leu
305                           310                       315                             320
Gln   Leu   Gly   Ile   Glu   Gly   Ala   Pro   Gln   Ala   Leu   Ser   Ile   Lys   Thr   Ser
                        325                       330                       335
Ser   Leu   Ala   Glu   Ala   Glu   Asn   Met   Ala   Asp   Leu   Ile   Asp   Gly   Tyr   Cys
                        340                       345                       350
Arg   Leu   Gln   Gly   Glu   His   Gln   Gly   Ser   Leu   Ile   Ile   His   Pro   Arg   Lys
            355                       360                       365
Asp   Gly   Glu   Lys   Arg   Asn   Ser   Leu   Pro   Gln   Ile   Pro   Met   Leu   Asn   Leu
            370                       375                       380
Glu   Ala   Arg   Arg   Ser   His   Leu   Ser   Glu   Ser   Cys   Ser   Ile   Glu   Ser   Asp
385                           390                       395                             400
Ile   Tyr   Ala   Glu   Ile   Pro   Asp   Glu   Thr   Leu   Arg   Arg   Pro   Gly   Gly   Pro
                        405                       410                       415
Gln   Tyr   Gly   Ile   Ala   Arg   Glu   Asp   Val   Val   Leu   Asn   Arg   Ile   Leu   Gly
                        420                       425                       430
```

| | | | | | | | | | | | | | | |
|---|---|---|---|---|---|---|---|---|---|---|---|---|---|---|
| Glu | Gly | Phe | Phe 435 | Gly | Glu | Val | Tyr | Glu 440 | Gly | Val | Tyr | Thr | Asn 445 | His | Lys |
| Gly | Glu | Lys 450 | Ile | Asn | Val | Ala 455 | Val | Lys | Thr | Cys | Lys 460 | Lys | Asp | Cys | Thr |
| Leu | Asp 465 | Asn | Lys | Glu | Lys | Phe 470 | Met | Ser | Glu | Ala | Val 475 | Ile | Met | Lys | Asn |
| Leu 480 | Asp | His | Pro | His 485 | Ile | Val | Lys | Leu | Ile 490 | Gly | Ile | Ile | Glu | Glu 495 |  |
| Pro | Thr | Trp | Ile | Ile 500 | Met | Glu | Leu | Tyr | Pro 505 | Tyr | Gly | Leu | Gly 510 | His |  |
| Tyr | Leu | Glu | Arg 515 | Asn | Lys | Asn | Ser | Leu 520 | Lys | Val | Leu | Thr | Leu 525 | Val | Leu |
| Tyr | Ser | Leu 530 | Gln | Ile | Cys | Lys | Ala 535 | Met | Ala | Tyr | Leu | Glu 540 | Ser | Ile | Asn |
| Cys | Val 545 | His | Arg | Asp | Ile | Ala 550 | Val | Arg | Asn | Ile | Leu 555 | Val | Ala | Ser | Pro |
| Glu 560 | Cys | Val | Lys | Leu | Gly 565 | Asp | Phe | Gly | Leu | Ser 570 | Arg | Tyr | Ile | Glu | Asp 575 |
| Glu | Asp | Tyr | Tyr | Lys 580 | Ala | Ser | Val | Thr | Arg 585 | Leu | Pro | Ile | Lys | Trp 590 | Met |
| Ser | Pro | Glu | Ser 595 | Ile | Asn | Phe | Arg | Arg 600 | Phe | Thr | Thr | Ala | Ser 605 | Asp | Val |
| Trp | Met | Phe | Ala 610 | Val | Cys | Met | Trp | Glu 615 | Ile | Leu | Ser | Phe | Gly 620 | Lys | Gln |
| Pro | Phe | Phe 625 | Trp | Leu | Glu | Asn | Lys 630 | Asp | Val | Ile | Gly | Val 635 | Leu | Glu | Lys |
| Gly | Asp 640 | Arg | Leu | Pro | Lys | Pro 645 | Asp | Leu | Cys | Pro | Pro 650 | Val | Leu | Tyr | Thr |
| Leu 655 | Met | Thr | Arg | Cys | Trp 660 | Asp | Tyr | Asp | Pro | Ser 665 | Asp | Arg | Pro | Arg | Phe 670 |
| Thr | Glu | Leu | Val | Cys 675 | Ser | Leu | Ser | Asp | Val 680 | Tyr | Gln | Met | Glu | Lys 685 | Asp |
| Ile | Ala | Met | Glu 690 | Gln | Glu | Arg | Asn | Ala 695 | Arg | Tyr | Arg | Thr | Pro 700 | Lys | Ile |
| Leu | Glu | Pro 705 | Thr | Ala | Phe | Gln | Glu 710 | Pro | Pro | Pro | Lys | Pro 715 | Ser | Arg | Pro |
| Lys | Tyr 720 | Arg | Pro | Pro | Gln | Thr 725 | Asn | Leu | Leu | Ala | Pro 730 | Lys | Leu | Gln |  |
| Phe 735 | Gln | Val | Pro | Glu | Gly 740 | Leu | Cys | Ala | Ser | Ser 745 | Pro | Thr | Leu | Thr | Ser 750 |
| Pro | Met | Glu | Tyr | Pro 755 | Ser | Pro | Val | Asn | Ser 760 | Leu | His | Thr | Pro | Pro 765 | Leu |
| His | Arg | His | Asn 770 | Val | Phe | Lys | Arg | His 775 | Ser | Met | Arg | Glu 780 | Glu | Asp | Phe |
| Ile | Gln | Pro 785 | Ser | Ser | Arg | Glu | Glu 790 | Ala | Gln | Gln | Leu | Trp 795 | Glu | Ala | Glu |
| Lys | Val 800 | Lys | Met | Arg | Gln | Ile 805 | Leu | Asp | Lys | Gln | Gln 810 | Lys | Gln | Met | Val |
| Glu 815 | Asp | Tyr | Gln | Trp | Leu 820 | Arg | Gln | Glu | Glu | Lys 825 | Ser | Leu | Asp | Pro | Met 830 |
| Val | Tyr | Met | Asn | Asp 835 | Lys | Ser | Pro | Leu | Thr 840 | Pro | Glu | Lys | Glu | Val 845 | Gly |
| Tyr | Leu | Glu | Phe 850 | Thr | Gly | Pro | Pro | Gln 855 | Lys | Pro | Pro | Arg | Leu 860 | Gly | Ala |

```
Gln  Ser  Ile  Gln  Pro  Thr  Ala  Asn  Leu  Asp  Arg  Thr  Asp    Asp  Leu  Val
          865                      870                     875

Tyr  Leu  Asn  Val  Met  Glu  Leu  Val  Arg  Ala  Val  Leu  Glu  Leu  Lys  Asn
     880                      885                     890

Glu  Leu  Cys  Gln  Leu  Pro  Pro  Glu  Gly  Tyr  Val  Val  Val  Lys  Asn
895                      900                     905                    910

Val  Gly  Leu  Thr  Leu  Arg  Lys  Leu  Ile  Gly  Ser  Val  Asp  Asp  Leu  Leu
               915                     920                    925

Pro  Ser  Leu  Pro  Ser  Ser  Ser  Arg  Thr  Glu  Ile  Glu  Gly  Thr  Gln  Lys
               930                    935                     940

Leu  Leu  Asn  Lys  Asp  Leu  Ala  Glu  Leu  Ile  Asn  Lys  Met  Arg  Leu  Ala
               945                    950                     955

Gln  Gln  Asn  Ala  Val  Thr  Ser  Leu  Ser  Glu  Glu  Cys  Lys  Arg  Gln  Met
          960                    965                     970

Leu  Thr  Ala  Ser  His  Thr  Leu  Ala  Val  Asp  Ala  Lys  Asn  Leu  Leu  Asp
975                      980                     985                    990

Ala  Val  Asp  Gln  Ala  Lys  Val  Leu  Ala  Asn  Leu  Ala  His  Pro  Pro  Ala
               995                    1000                    1005

Glu
```

( 2 ) INFORMATION FOR SEQ ID NO: 2:

( i ) SEQUENCE CHARACTERISTICS:
        ( A ) LENGTH: 3416
        ( B ) TYPE: nucleic acid
        ( C ) STRANDEDNESS: single
        ( D ) TOPOLOGY: linear ( i i ) MOLECULE TYPE: nucleic ( x i ) SEQUENCE DESCRIPTION: SEQ ID NO: 2:

```
CGGTACAGGT  AAGTCGGCCG  GGCAGGTAGG  GGTGCCCGAG  GAGTAGTCGC  TGGAGTCCGC     60

GCCTCCCTGG  GACTGCAATG  TGCCGGTCTT  AGCTGCTGCC  TGAGAGGATG  TCTGGGGTGT    120

CCGAGCCCCT  GAGCCGAGTA  AAGTTGGGCA  CATTACGCCG  GCCTGAAGGC  CCTGCAGAGC    180

CCATGGTGGT  GGTACCAGTA  GATGTGGAAA  AGGAGGACGT  GCGTATCCTC  AAGGTCTGCT    240

TCTATAGCAA  CAGCTTCAAT  CCTGGGAAGA  ACTTCAAACT  GGTCAAATGC  ACTGTCCAGA    300

CGGAGATCCG  GGAGATCATC  ACCTCCATCC  TGCTGAGCGG  GCGGATCGGG  CCCAACATCC    360

GGTTGGCTGA  GTGCTATGGG  CTGAGGCTGA  AGCACATGAA  GTCCGATGAG  ATCCACTGGC    420

TGCACCCACA  GATGACGGTG  GGTGAGGTGC  AGGACAAGTA  TGAGTGTCTG  CACGTGGAAG    480

CCGAGTGGAG  GTATGACCTT  CAAATCCGCT  ACTTGCCAGA  AGACTTCATG  GAGAGCCTGA    540

AGGAGGACAG  GACCACGCTG  CTCTATTTTT  ACCAACAGCT  CCGGAACGAC  TACATGCAGC    600

GCTACGCCAG  CAAGGTCAGC  GAGGGCATGG  CCCTGCAGCT  GGGCTGCCTG  GAGCTCAGGC    660

GGTTCTTCAA  GGATATGCCC  CACAATGCAC  TTGACAAGAA  GTCCAACTTC  GAGCTCCTAG    720

AAAAGGAAGT  GGGGCTGGAC  TTGTTTTTCC  CAAAGCAGAT  GCAGGAGAAC  TTAAAGCCCA    780

AACAGTTCCG  GAAGATGATC  CAGCAGACCT  TCCAGCAGTA  CGCCTCGCTC  AGGGAGGAGG    840

AGTGCGTCAT  GAAGTTCTTC  AACACTCTCG  CCGGCTTCGC  CAACATCGAC  CAGGAGACCT    900

ACCGCTGTGA  ACTCATTCAA  GGATGGAACA  TTACTGTGGA  CCTGGTCATT  GGCCCTAAAG    960

GGATCCGCCA  GCTGACTAGT  CAGGACGCAA  AGCCCACCTG  CCTGGCCGAG  TTCAAGCAGA   1020

TCAGGTCCAT  CAGGTGCCTC  CCGCTGGAGG  AGGGCCAGGC  AGTACTTCAG  CTGGGCATTG   1080

AAGGTGCCCC  CCAGGCCTTG  TCCATCAAAA  CCTCATCCCT  AGCAGAGGCT  GAGAACATGG   1140
```

```
CTGACCTCAT  AGACGGCTAC  TGCCGGCTGC  AGGGTGAGCA  CCAAGGCTCT  CTCATCATCC    1200
ATCCTAGGAA  AGATGGTGAG  AAGCGGAACA  GCCTGCCCCA  GATCCCCATG  CTAAACCTGG    1260
AGGCCCGGCG  GTCCCACCTC  TCAGAGAGCT  GCAGCATAGA  GTCAGACATC  TACGCAGAGA    1320
TTCCCGACGA  AACCCTGCGA  AGGCCCGGAG  GTCCACAGTA  TGGCATTGCC  CGTGAAGATG    1380
TGGTCCTGAA  TCGTATTCTT  GGGGAAGGCT  TTTTGGGGA   GGTCTATGAA  GGTGTCTACA    1440
CAAATCACAA  AGGGGAGAAA  ATCAATGTAG  CTGTCAAGAC  CTGCAAGAAA  GACTGCACTC    1500
TGGACAACAA  GGAGAAGTTC  ATGAGCGAGG  CAGTGATCAT  GAAGAACCTC  GACCACCCGC    1560
ACATCGTGAA  GCTGATCGGC  ATCATTGAAG  AGGAGCCCAC  CTGGATCATC  ATGGAATTGT    1620
ATCCCTATGG  GGAGCTGGGC  CACTACCTGG  AGCGGAACAA  GAACTCCCTG  AAGGTGCTCA    1680
CCCTCGTGCT  GTACTCACTG  CAGATATGCA  AAGCCATGGC  CTACCTGGAG  AGCATCAACT    1740
GCGTGCACAG  GGACATTGCT  GTCCGGAACA  TCCTGGTGGC  CTCCCCTGAG  TGTGTGAAGC    1800
TGGGGGACTT  TGGTCTTTCC  CGGTACATTG  AGGACGAGGA  CTATTACAAA  GCCTCTGTGA    1860
CTCGTCTCCC  CATCAAATGG  ATGTCCCAG   AGTCCATTAA  CTTCCGACGC  TTCACGACAG    1920
CCAGTGACGT  CTGGATGTTC  GCCGTGTGCA  TGTGGGAGAT  CCTGAGCTTT  GGGAAGCAGC    1980
CCTTCTTCTG  GCTGGAGAAC  AAGGATGTCA  TCGGGGTGCT  GGAGAAAGGA  GACCGGCTGC    2040
CCAAGCCTGA  TCTCTGTCCA  CCGGTCCTTT  ATACCCTCAT  GACCCGCTGC  TGGGACTACG    2100
ACCCCAGTGA  CCGGCCCCGC  TTCACCGAGC  TGGTGTGCAG  CCTCAGTGAC  GTTTATCAGA    2160
TGGAGAAGGA  CATTGCCATG  GAGCAAGAGA  GGAATGCTCG  CTACCGAACC  CCCAAAATCT    2220
TGGAGCCCAC  AGCCTTCCAG  GAACCCCAC   CCAAGCCCAG  CCGACCTAAG  TACAGACCCC    2280
CTCCGCAAAC  CAACCTCCTG  GCTCCAAAGC  TGCAGTTCCA  GGTTCCTGAG  GGTCTGTGTG    2340
CCAGCTCTCC  TACGCTCACC  AGCCCTATGG  AGTATCCATC  TCCCGTTAAC  TCACTGCACA    2400
CCCCACCTCT  CCACCGGCAC  AATGTCTTCA  AACGCCACAG  CATGCGGGAG  GAGGACTTCA    2460
TCCAACCCAG  CAGCCGAGAA  GAGGCCCAGC  AGCTGTGGGA  GGCTGAAAAG  GTCAAAATGC    2520
GGCAAATCCT  GGACAAACAG  CAGAAGCAGA  TGGTGGAGGA  CTACCAGTGG  CTCAGGCAGG    2580
AGGAGAAGTC  CCTGGACCCC  ATGGTTTATA  TGAATGATAA  GTCCCCATTG  ACGCCAGAGA    2640
AGGAGGTCGG  CTACCTGGAG  TTCACAGGGC  CCCCACAGAA  GCCCCCGAGG  CTGGGCGCAC    2700
AGTCCATCCA  GCCCACAGCT  AACCTGGACC  GGACCGATGA  CCTGGTGTAC  CTCAATGTCA    2760
TGGAGCTGGT  GCGGGCCGTG  CTGGAGCTCA  AGAATGAGCT  CTGTCAGCTG  CCCCCCGAGG    2820
GCTACGTGGT  GGTGGTGAAG  AATGTGGGGC  TGACCCTGCG  GAAGCTCATC  GGGAGCGTGG    2880
ATGATCTCCT  GCCTTCCTTG  CCGTCATCTT  CACGGACAGA  GATCGAGGGC  ACCCAGAAAC    2940
TGCTCAACAA  AGACCTGGCA  GAGCTCATCA  ACAAGATGCG  GCTGGCGCAG  CAGAACGCCG    3000
TGACCTCCCT  GAGTGAGGAG  TGCAAGAGGC  AGATGCTGAC  GGCTTCACAC  ACCCTGGCTG    3060
TGGACGCCAA  GAACCTGCTC  GACGCTGTGG  ACCAGGCCAA  GGTTCTGGCC  AATCTGGCCC    3120
ACCCACCTGC  AGAGTGACGG  AGGGTGGGGG  CCACCTGCCT  GCGTCTTCCG  CCCCTGCCTG    3180
CCATGTACCT  CCCCTGCCTT  GCTGTTGGTC  ATGTGGGTCT  TCCAGGGAGA  AGGCCAAGGG    3240
GAGTCACCTT  CCCTTGCCAC  TTTGCACGAC  GCCCTCTCCC  CACCCCTACC  CCTGGCTGTA    3300
CTGCTCAGGC  TGCAGCTGGA  CAGAGGGGAC  TCTGGGCTAT  GGACACAGGG  TGACGGTGAC    3360
AAAGATGGCT  CAGAGGGGGA  CTGCTGCTGC  CTGGCCACTG  CTCCCTAAGC  CAGCCT        3416
```

( 2 ) INFORMATION FOR SEQ ID NO: 3:

( i ) SEQUENCE CHARACTERISTICS:
    ( A ) LENGTH: 9
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 3:

Ile His Arg Asp Leu Ala Ala Arg Asn
               5

( 2 ) INFORMATION FOR SEQ ID NO: 4:

( i ) SEQUENCE CHARACTERISTICS:
    ( A ) LENGTH: 8
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 4:

Trp Met Phe Gly Val Thr Leu Trp
             5

( 2 ) INFORMATION FOR SEQ ID NO: 5:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( i i ) SEQUENCE DESCRIPTION: SEQ ID NO: 5:

CGGGATCCTC ATCATCCATC CTAGGAAAGA    30

( 2 ) INFORMATION FOR SEQ ID NO: 6:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( i i ) SEQUENCE DESCRIPTION: SEQ ID NO: 6:

CGGGAATTCG TCGTAGTCCC AGCAGCGGGT    30

( 2 ) INFORMATION FOR SEQ ID NO: 7:

( i ) SEQUENCE CHARACTERISTICS:
    ( A ) LENGTH: 10
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 7:

Tyr Pro Tyr Asp Val Pro Asp Tyr Ala Ser
               5                 10

( 2 ) INFORMATION FOR SEQ ID NO: 8:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) SEQUENCE DESCRIPTION: SEQ ID NO: 8:

CACAATGTCT TCAAACGCCA C    21

( 2 ) INFORMATION FOR SEQ ID NO: 9:

( i ) SEQUENCE CHARACTERISTICS:
        ( A ) LENGTH: 63
        ( B ) TYPE: nucleic acid
        ( C ) STRANDEDNESS: single
        ( D ) TOPOLOGY: linear ( i i ) SEQUENCE DESCRIPTION: SEQ ID NO: 9:

GGCTCTAGAT CACGATGCGT AGTCAGGGAC ATCGTATGGG RACTCTGCAG GTGGGTGGGC    60

CAG    63

( 2 ) INFORMATION FOR SEQ ID NO: 10:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 10:

CAATGTAGCT GTCGCGACCT GCAAGAAAGA C    31

( 2 ) INFORMATION FOR SEQ ID NO: 11:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION: SEQ ID NO: 11:

GCCAGCAGGC CATGTCACTG G    21

( 2 ) INFORMATION FOR SEQ ID NO: 12:

( i ) SEQUENCE CHARACTERISTICS:
        ( A ) LENGTH: 60
        ( B ) TYPE: nucleic acid
        ( C ) STRANDEDNESS: single
        ( D ) TOPOLOGY: linear ( i i ) SEQUENCE DESCRIPTION: SEQ ID NO: 12:

CGGAATTCTT ACGATGCGTA GTCAGGGACA TCGTATGGGT AGACATCAGT TAACATTTTG    60

( 2 ) INFORMATION FOR SEQ ID NO: 13:

( i ) SEQUENCE CHARACTERISTICS:
        ( A ) LENGTH: 9
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 13:

Ile His Arg Asp Leu Ala Ala Arg Asn
                  5

( 2 ) INFORMATION FOR SEQ ID NO: 14:

( i ) SEQUENCE CHARACTERISTICS:
        ( A ) LENGTH: 8
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO: 14:

Trp Met Phe Gly Val Thr Leu Trp
                  5

(2) INFORMATION FOR SEQ ID NO: 15:

(i) SEQUENCE CHARACTERISTICS:
   (A) LENGTH: 4
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO: 15:

Tyr Leu Met Val (2) INFORMATION FOR SEQ ID NO: 16:

(i) SEQUENCE CHARACTERISTICS:
   (A) LENGTH: 4
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO: 16:

Tyr Val Val Val

PYK2 RELATED POLYNUCLEOTIDE PRODUCTS

FIELD OF THE INVENTION

The present invention relates generally to the fields of biology, biochemistry and medicine and more specifically to the field of cellular signal transduction.

BACKGROUND OF THE INVENTION

None of the following discussion of the background of the invention is admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of tyrosine residues on proteins. The phosphorylation state of a protein is modified through the reciprocal actions of tyrosine phosphatases (TPs) and tyrosine kinases (TKs), including receptor tyrosine kinases and non-receptor tyrosine kinases.

Receptor tyrosine kinases (RTKs) belong to a family of transmembrane proteins and have been implicated in cellular signaling pathways. The predominant biological activity of some RTKs is the stimulation of cell growth and proliferation, while other RTKs are involved in arresting growth and promoting differentiation. In some instances, a single tyrosine kinase can inhibit, or stimulate, cell proliferation depending on the cellular environment in which it is expressed.

RTKs are composed of at least three domains: an extracellular ligand binding domain, a transmembrane domain and a cytoplasmic catalytic domain that can phosphorylate tyrosine residues. Ligand binding to membrane-bound receptors induces the formation of receptor dimers and allosteric changes that activate the intracellular kinase domains and result in the self-phosphorylation (autophosphorylation and/or transphosphorylation) of the receptor on tyrosine residues. Individual phosphotyrosine residues of the cytoplasmic domains of receptors may serve as specific binding sites that interact with a host of cytoplasmic signaling molecules, thereby activating various signal transduction pathways.

The intracellular, cytoplasmic, non-receptor protein tyrosine kinases do not contain a hydrophobic transmembrane domain or an extracellular domain and share non-catalytic domains in addition to sharing their catalytic kinase domains. Such non-catalytic domains include the SH2 domains and SH3 domains. The non-catalytic domains are thought to be important in the regulation of protein-protein interactions during signal transduction.

A central feature of signal transduction is the reversible phosphorylation of certain proteins. Receptor phosphorylation stimulates a physical association of the activated receptor with target molecules, which either are or are not phosphorylated.

Some of the target molecules such as phospholipase Cγ are in turn phosphorylated and activated. Such phosphorylation transmits a signal to the cytoplasm. Other target molecules are not phosphorylated, but assist in signal transmission by acting as adapter molecules for secondary signal transducer proteins. For example, receptor phosphorylation and the subsequent allosteric changes in the receptor recruit the Grb-2/SOS complex to the catalytic domain of the receptor where its proximity to the membrane allows it to activate ras.

The secondary signal transducer molecules generated by activated receptors result in a signal cascade that regulates cell functions such as cell division or differentiation. Reviews describing intracellular signal transduction include Aaronson, *Science*, 254:1146–1153, 1991; Schlessinger, *Trends Biochem. Sci.*, 13:443–47, 1988; and Ullrich and Schlessinger, *Cell*, 61:203–212, 1990.

Signal transduction pathways that regulate ion channels (e.g., potassium channels and calcium channels) involve G proteins which function as intermediaries between receptors and effectors. Gilman, *Ann. Rev. Biochem.*, 56:615–649 (1987); Brown and Birnbaumer, *Ann. Rev. Physiol.*, 52:197–213 (1990). G-coupled protein receptors are receptors for neurotransmitters, ligands that are responsible for signal production in nerve cells as well as for regulation of proliferation and differentiation of nerves and other cell types. Neurotransmitter receptors exist as different subtypes which are differentially expressed in various tissues and neurotransmitters such as acetylcholine evoke responses throughout the central and peripheral nervous systems.

The muscarinic acetylcholine receptors play important roles in a variety of complex neural activities such as learning, memory, arousal and motor and sensory modulation. These receptors have also been implicated in several central nervous system disorders such as Alzheimer's disease, Parkinson's disease, depression and schizophrenia.

Some agents that are involved in a signal transduction pathway regulating one ion channel, for example a potassium channel, may also be involved in one or more other pathways regulating one or more other ion channels, for example a calcium channel. Dolphin, *Ann. Rev. Physiol.*, 52:243–55 (1990); Wilk-Blaszczak et al., *Neuron*, 12:109–116 (1994). Ion channels may be regulated either with or without a cytosolic second messenger. Hille, *Neuron*, 9:187–195 (1992). One possible cytosolic second messenger is a tyrosine kinase. Huang et al., *Cell*, 75:1145–1156 (1993), incorporated herein by reference in its entirety, including any drawings.

The receptors involved in the signal transduction pathways that regulate ion channels are ultimately linked to the ion channels by various intermediate events and agents. For example, such events include an increase in intracellular calcium and inositol triphosphate and production of endothelin. Frucht, et al., *Cancer Research*, 52:1114–1122 (1992); Schrey, et al., *Cancer Research*, 52:1786–1790 (1992). Intermediary agents include bombesin, which stimulates DNA synthesis and the phosphorylation of a specific protein kinase C substrate. Rodriguez-Pena, et al., *Biochemical and Biophysical Research Communication*, 140(1):379–385 (1986); Fisher and Schonbrunn, *The Journal of Biological Chemistry*, 263(6):2208–2816 (1988).

Focal adhesion kinase (FAK) is a cytoplasmic protein tyrosine kinase localized to focal adhesions that is known to associate with two Src family kinases. Schaller, et al., *Proc. Natl. Acad. Sci. U.S.A.*, 89:5192–5196 (1992), incorporated herein by reference in its entirety, including any drawings; Cobb et al., *Molecular and Cellular Biology*, 14(1):147–155 (1994). The proteins associated with the cytoplasmic surface of adhesion molecules are reviewed in Gumbiner, *Neuron*, 11:551–564 (1993).

FAK may regulate interactions of integrins, agonist receptors, and/or stress fibers. Shattil et al., *The Journal of Biological Chemistry*, 269(20):14738–14745 (1994); Ridley and Hall, *The EMBO Journal*, 13(11):2600–2610 (1994). FAK does not contain SH2 or SH3 domains and the amino acid sequence of FAK is highly conserved among birds, rodents and man.

In some cells the C-terminal domain of FAK is expressed autonomously as a 41 kDa protein called FRNK and the 140 C-terminal residues of FAK contain a focal adhesion targeting (FAT) domain. The cDNA's encoding FRNK are given in Schaller et al., *Molecular and Cellular Biology*, 13(2):785–791 (1993), incorporated herein by reference in its entirety, including any drawings. The FAT domain was identified and said to be required for localization of FAK to cellular focal adhesions in Hilderbrand et al., *The Journal of Cell Biology*, 123(4):993–1005 (1993).

SUMMARY OF THE INVENTION

The present invention relates to PYK2 polypeptides, nucleic acids encoding such polypeptides, cells, tissues and animals containing such polypeptides and nucleic acids, antibodies to such polypeptides, assays utilizing such polypeptides, and methods relating to all of the foregoing. PYK2 polypeptides are involved in various signal transduction pathways and thus the present invention provides several agents and methods useful for diagnosing, treating, and preventing various diseases or conditions associated with abnormalities in these pathways.

The present invention is based upon the identification and isolation of a novel non-receptor tyrosine kinase, termed PYK2, that is activated by binding of ligand to G-coupled protein receptors such as bradykinin and acetylcholine. PYK2 has a predicted molecular weight of 111 kD and contains five domains: (1) a relatively long N-terminal domain; (2) a kinase catalytic domain; (3) a proline rich domain; (4) another proline rich domain; and (5) a C-terminal focal adhesion targeting (FAT) domain. PYK2 does not contain a SH2 or SH3 domain.

The FAT domain of PYK2 has 62% similarity to the FAT domain of another non-receptor tyrosine kinase, FAK, which is also activated by G-coupled proteins. The overall similarity between PYK2 and FAK is 52%. PYK2 is expressed principally in neural tissues, although expression can also be detected in hematopoietic cells at early stages of development and in some tumor cell lines. The expression of PYK2 does not correspond with the expression of FAK.

PYK2 is believed to regulate the activity of potassium channels in response to neurotransmitter signalling. PYK2 enzymatic activity is positively regulated by phosphorylation on tyrosine and results in response to binding of bradykinin, TPA, calcium ionophore, carbachol, TPA+ forskolin, and membrane depolarization. The combination of toxins known to positively regulate G-coupled receptor signalling (such as pertusis toxin, cholera toxins, TPA and bradykinin) increases the phosphorylation of PYK2.

Activated PYK2 phosphorylates RAK, a delayed rectifier type potassium channel, and thus suppresses RAK activity. In the same system, FAK does not phosphorylate RAK. PYK2 is responsible for regulating neurotransmitter signalling and thus may be used to treat conditions of nervous system by enhancing or inhibiting such signalling.

Thus, in a first aspect the invention features an isolated, purified, enriched or recombinant nucleic acid encoding a PYK2 polypeptide.

By "isolated" in reference to nucleic acid is meant a polymer of 2 (preferably 21, more preferably 39, most preferably 75) or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only nucleotide chain present, but does indicate that it is the predominate sequence present (at least 10–20% more than any other nucleotide sequence) and is essentially free (about 90–95% pure at least) of non-nucleotide material naturally associated with it. Therefore, the term does not encompass an isolated chromosome encoding a PYK2 polypeptide.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased in a useful manner and preferably separate from a sequence library. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "a PYK2 polypeptide" is meant two or more contiguous amino acids set forth in the full length amino acid sequence of SEQ ID NO:1. The PYK2 polypeptide can be encoded by a full-length nucleic acid sequence or any portion of the full-length nucleic acid sequence, so long as a functional activity of the polypeptide is retained. Preferred functional activities include the ability to phosphorylate and regulate RAK and/or other potassium channels.

In preferred embodiments the isolated nucleic acid comprises, consists essentially of, or consists of a nucleic acid sequence set forth in the full length nucleic acid sequence SEQ ID NO:2 or at least 27, 30, 35, 40 or 50 contiguous nucleotides thereof and the PYK2 polypeptide comprises, consists essentially of, or consists of at least 9, 10, 15, 20, or 30 contiguous amino acids of a PYK2 polypeptide.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Compositions and probes of the present invention may contain human nucleic acid encoding a PYK-2 polypeptide but are substantially free of nucleic acid not encoding a human PYK-2 polypeptide. The human nucleic acid encoding a PYK-2 polypeptide is at least 18 contiguous bases of the nucleotide sequence set forth in SEQ ID NO 2 and will selectively hybridize to human genomic DNA encoding a PYK-2 polypeptide, or is complementary to such a sequence. The nucleic acid may be isolated from a natural source by cDNA cloning or subtractive hybridization; the natural source may be blood, semen, and tissue of various organisms including eukaryotes, mammals, birds, fish, plants, gorillas, rhesus monkeys, chimpanzees and humans; and the nucleic acid may be synthesized by the triester method or by using an automated DNA synthesizer. In yet other preferred embodiments the nucleic acid is a conserved or unique region, for example those useful for the design of hybridization probes to facilitate identification and cloning of additional polypeptides, the design of PCR probes to facilitate cloning of additional polypeptides, and obtaining antibodies to polypeptide regions.

By "conserved nucleic acid regions", are meant regions present on two or more nucleic acids encoding a PYK2 polypeptide, to which a particular nucleic acid sequence can hybridize to under lower stringency conditions. Examples of lower stringency conditions suitable for screening for nucleic acid encoding PYK2 polypeptides are provided in Abe, et al. *J. Biol. Chem.*, 19:13361 (1992) (hereby incorporated by reference herein in its entirety, including any drawings). Preferably, conserved regions differ by no more than 7 out of 20 nucleotides.

By "unique nucleic acid region" is meant a sequence present in a full length nucleic acid coding for a PYK2 polypeptide that is not present in a sequence coding for any other naturally occurring polypeptide. Such regions preferably comprise 12 or 20 contiguous nucleotides present in the full length nucleic acid encoding a PYK2 polypeptide.

The invention also features a nucleic acid probe for the detection of a PYK2 polypeptide or nucleic acid encoding a PYK2 polypeptide in a sample. The nucleic acid probe contains nucleic acid that will hybridize to a sequence set forth in SEQ ID NO:2.

In preferred embodiments the nucleic acid probe hybridizes to nucleic acid encoding at least 12, 27, 30, 35, 40 or 50 contiguous amino acids of the full-length sequence set forth in SEQ ID NO:1. Various low or high stringency hybridization conditions may be used depending upon the specificity and selectivity desired.

By "high stringency hybridization conditions" is meant those hybridizing conditions that (1) employ low ionic strength and high temperature for washing, for example, 0.015M NaCl/0.0015M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75M NaCl, 0.075M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS. Under stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount PYK2 RNA in a sample by contacting the sample with a nucleic acid probe under conditions such that hybridization occurs and detecting the presence or amount of the probe bound to PYK2 RNA. The nucleic acid duplex formed between the probe and a nucleic acid sequence coding for a PYK2 polypeptide may be used in the identification of the sequence of the nucleic acid detected (for example see, Nelson et al., in *Nonisotopic DNA Probe Techniques*, p. 275 Academic Press, San Diego (Kricka, ed., 1992) hereby incorporated by reference herein in its entirety, including any drawings). Kits for performing such methods may be constructed to include a container means having disposed therein a nucleic acid probe.

The invention also features recombinant nucleic acid, preferably in a cell or an organism. The recombinant nucleic acid may contain a sequence set forth in SEQ ID NO:2 and a vector or a promoter effective to initiate transcription in a host cell. The recombinant nucleic acid can alternatively contain a transcriptional initiation region functional in a cell, a sequence complimentary to an RNA sequence encoding a PYK2 polypeptide and a transcriptional termination region functional in a cell.

In another aspect the invention features an isolated, enriched or purified PYK2 polypeptide.

By "isolated" in reference to a polypeptide is meant a polymer of 2 (preferably 7, more preferably 13, most preferably 25) or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is the predominate sequence present (at least 10–20% more than any other sequence) and is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19.

The term is meant to cover only those situations in which man has intervened to elevate the proportion of the desired amino acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments the PYK-2 polypeptide contains at least 9, 10, 15, 20, or 30 contiguous amino acids of the full-length sequence set forth in SEQ ID NO:1.

In yet another aspect the invention features a purified antibody (e.g., a monoclonal or polyclonal antibody) having specific binding affinity to a PYK2 polypeptide. The antibody contains a sequence of amino acids that is able to specifically bind to a PYK2 polypeptide.

By "specific binding affinity" is meant that the antibody will bind to a PYK-2 polypeptide at a certain detectable amount but will not bind other polypeptides, such as FAK polypeptides to the same extent, under identical conditions.

Antibodies having specific binding affinity to a PYK2 polypeptide may be used in methods for detecting the presence and/or amount of a PYK2 polypeptide in a sample by contacting the sample with the antibody under conditions such that an immunocomplex forms and detecting the presence and/or amount of the antibody conjugated to the PYK2 polypeptide. Diagnostic kits for performing such methods may be constructed to include a first container means containing the antibody and a second container means having a conjugate of a binding partner of the antibody and a label.

In another aspect the invention features a hybridoma which produces an antibody having specific binding affinity to a PYK2 polypeptide.

By "hybridoma" is meant an immortalized cell line which is capable of secreting an antibody, for example a PYK2 antibody.

In preferred embodiments the PYK2 antibody comprises a sequence of amino acids that is able to specifically bind a PYK2 polypeptide.

Another aspect of the invention features a method of detecting the presence or amount of a compound capable of binding to a PYK2 polypeptide. The method involves incubating the compound with a PYK2 polypeptide and detecting the presence or amount of the compound bound to the PYK2 polypeptide.

In preferred embodiments, the compound inhibits a phosphorylation activity of PYK2 and is selected from the group consisting of tyrphostins, quinazolines, quinaxolines, and quinolines. The present invention also features compounds capable of binding and inhibiting PYK2 polypeptide that are identified by methods described above.

In another aspect the invention features a method of screening potential agents useful for treatment of a disease or condition characterized by an abnormality in a signal transduction pathway that contains an interaction between a PYK2 polypeptide and a natural binding partner (NBP). The method involves assaying potential agents for those able to promote or disrupt the interaction as an indication of a useful agent.

By "screening" is meant investigating an organism for the presence or absence of a property. The process may include measuring or detecting various properties, including the level of signal transduction and the level of interaction between a PYK2 polypeptide and a NBP.

By "disease or condition" is meant a state in an organism, e.g., a human, which is recognized as abnormal by members of the medical community. The disease or condition may be characterized by an abnormality in one or more signal transduction pathways in a cell, preferably a cell listed in table 1, wherein one of the components of the signal transduction pathway is either a PYK2 polypeptide or a NBP.

TABLE 1

| CELL LINE | CHECKED BY | LEVEL OF EX- PRESSION | COMMENT |
|---|---|---|---|
| NIH3T3 | IP/IB | – | High expression of Fak (IP/IB) |
| L cells | IP/IB | – | — |
| Jurkat (T-lymphoblastic cells) | IP/IB | + | very high expression of Fak (IP/IB) |
| KG-1 (human myeloblast/ promyelocte) | IP/IB | +++ | — |
| K562 (human erythroleukemia) | IP/IB | ++ | — |
| CHRF (premegakaryocyte, human) | IP/IB | +++ | After differentiation with TPA for 3 days, mobility shift of PYK2 |
| L8057 (premegakaryocyte, mouse) | IP/IB | ++ | After differentiation with TPA for 3 days, mobility shift of PYK2 |
| T47D (human breast carcinoma) | IP/IB, PCR | ++ | PCR gave higher expression as compared to the IP/IB |
| GH3 (Pituitary tumor, rat) | IP/IB | ++ | — |
| PC12 | IP/IB, PCR, Northern | +++ | No change of PYK2 expression level or mobility after 36 hr treatment with NGF, |

TABLE 1-continued

| CELL LINE | CHECKED BY | LEVEL OF EX- PRESSION | COMMENT |
| --- | --- | --- | --- |
| XC (Sarcoma, rat) | IP/IB | +++ | No expression of Fak (IP/IB) PYK2 is phosphorylated on tyrosine |
| HEL (human erythroleukemia /myeloid) | IP/IB | ++ | — |
| HL-60 (human promyelocytic leukemia) | IP/IB | ++++ | — |
| NG108-15 (neuroblastoma- glioma hybrid) | IP/IB | + | — |

Specific diseases or disorders which might be treated or prevented, based upon the affected cells include: myasthenia gravis; neuroblastoma; disorders caused by neuronal toxins such as cholera toxin, pertusis toxin, or snake venom; acute megakaryocytic myelosis; thrombocytopenia; those of the central nervous system such as seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome. Conditions that may be treated by PYK2 inhibitors include epilepsy, schizophrenia, extreme hyperactivity in children, chronic pain, and acute pain. Examples of conditions that may be treated by PYK2 enhancers (for example a phosphatase inhibitor) include stroke, Alzheimer's, Parkinson's, other neurodegenerative diseases and migraine.

Preferred disorders include epilepsy, stroke, schizophrenia, and Parkinson's disorder as there is an established relationship between these disorders and the function of potassium channels. See, McLean et al., *Epilepsia* 35:S5–S9 1994; Ricard-Mousnier et al., *Neurophysiologie Clinique* 23:395–421, 1993; *Crit Rev. Veurobiol* 7:187–203, 1994; Simon and Lin, *Biophys. J.* 64:A100, 1993; Birnstiel et al., *Synapse* (N.Y.) 11:191–196, 1992; Coleman et al., *Brain Res.* 575:138–142 1992; Popolip et al., *Br. J. Pharmacol* 104:907–913, 1991; Murphy et al., *Exp. Brain Res.* 84:355–358, 1991; Rutecki et al., *Epilepsia* 32:1–2, 1991; Fisher and Coyle (ed), *Frontiers of Clinical Neurosciene*, Vol. 11 "Neurotransmitters and Epilepsy"; Meeting, Woods Hole Mass., USA IX+260P. John Wiley and Sons, Inc. N.Y., N.Y.; Treherne and Ashford, *Neuroscience* 40:523–532, 1991; Gehlert, *Prog. Neuro-Psychopharmacol. Biol. Psychiatry* 18:1093–1102, 1994; Baudy, *Expert Opin Ther. Pat.* 1994 4/4:343–378; Porter and Rogawski, *Epilepsia* 33:S1–S6, 1992; Murphy, *J. Physiol.* 453:167–183, 1992; Cromakalim, *Drugs Future* 17/3:237–239, 1992; Carmeliet, *Eur. Heart J.* 12:30–37, 1991; Olpe et al., *Experientia* 47/3:254–257, 1991; Andrade et al., *Science* 234/ 4781:1261–1265, 1986; Forster, *J. Neurosci. Methods* 13/3–4:199–212, 1985.

In preferred embodiments, the methods described herein involve identifying a patient in need of treatment. Those skilled in the art will recognize that various techniques may be used to identify such patients. For example, cellular potassium levels may be measured or the individuals' genes may be examined for a defect.

By "abnormality" is meant a level which is statistically different from the level observed in organisms not suffering from such a disease or condition and may be characterized as either an excess amount, intensity or duration of signal or a deficient amount, intensity or duration of signal. The abnormality in signal transduction may be realized as an abnormality in cell function, viability or differentiation state. We have determined that such abnormality in a pathway can be alleviated by action at the PYK2:NBP interaction site in the pathway. An abnormal interaction level may also either be greater or less than the normal level and may impair the normal performance or function of the organism. Thus, it is also possible to screen for agents that will be useful for treating a disease or condition, characterized by an abnormality in the signal transduction pathway, by testing compounds for their ability to affect the interaction between a PYK2 polypeptide and a NBP, since the complex formed by such interaction is part of the signal transduction pathway.

However, the disease or condition may be characterized by an abnormality in the signal transduction pathway even if the level of interaction between the PYK2 polypeptide and NBP is normal.

By "interact" is meant any physical association between polypeptides, whether covalent or non-covalent. This linkage can include many chemical mechanisms, for instance covalent binding, affinity binding, intercalation, coordinate binding and complexation. Examples of non-covalent bonds include electrostatic bonds, hydrogen bonds, and Van der Waals bonds. Furthermore, the interactions between polypeptides may either be direct or indirect. Thus, the association between two given polypeptides may be achieved with an intermediary agent, or several such agents, that connects the two proteins of interest (e.g., a PYK2 polypeptide and a NBP). Another example of an indirect interaction is the independent production, stimulation, or inhibition of both a PYK2 polypeptide and NBP by a regulatory agent. Depending upon the type of interaction present, various methods may be used to measure the level of interaction. For example, the strengths of covalent bonds are often measured in terms of the energy required to break a certain number of bonds (i.e., kcal/mol) Non-covalent interactions are often described as above, and also in terms of the distance between the interacting molecules. Indirect interactions may be described in a number of ways, including the number of intermediary agents involved, or the degree of control exercised over the PYK2 polypeptide relative to the control exercised over the NBP.

By "disrupt" is meant that the interaction between the PYK2 polypeptide and NBP is reduced either by preventing expression of the PYK2 polypeptide, or by preventing expression of the NBP, or by specifically preventing interaction of the naturally synthesized proteins or by interfering with the interaction of the proteins.

By "promote" is meant that the interaction between a PYK2 polypeptide and NBP is increased either by increasing expression of a PYK2 polypeptide, or by increasing expression of a NBP, or by decreasing the dephosphorylating activity of the corresponding regulatory TP (or other phosphatase acting on other phosphorylated signalling components) by promoting interaction of the PYK2 polypeptide and NBP or by prolonging the duration of the interaction. Covalent binding can be promoted either by direct condensation of existing side chains or by the incorporation of external bridging molecules. Many bivalent or polyvalent linking agents are useful in coupling polypeptides, such as an antibody, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, *J. Immunol.* 133:1335–2549; Jansen, F. K., et al., 1982, *Immunological Rev.* 62:185–15 216; and Vitetta et al., supra).

By "NBP" is meant a natural binding partner of a PYK2 polypeptide that naturally associates with a PYK2 polypeptide. The structure (primary, secondary, or tertiary) of the particular natural binding partner will influence the particular type of interaction between the PYK2 polypeptide and the natural binding partner. For example, if the natural binding partner comprises a sequence of amino acids complementary to the PYK2 polypeptide, covalent bonding may be a possible interaction. Similarly, other structural characteristics may allow for other corresponding interactions. The interaction is not limited to particular residues and specifically may involve phosphotyrosine, phosphoserine, or phosphothreonine residues. A broad range of sequences may be capable of interacting with PYK2 polypeptides. Using techniques well known in the art, one may identify several natural binding partners for PYK2 polypeptides.

By "signal transduction pathway" is meant the sequence of events that involves the transmission of a message from an extracellular protein to the cytoplasm through a cell membrane. The signal ultimately will cause the cell to perform a particular function, for example, to uncontrollably proliferate and therefore cause cancer. Various mechanisms for the signal transduction pathway (Fry et al., *Protein Science*, 2:1785–1797, 1993) provide possible methods for measuring the amount or intensity of a given signal. Depending upon the particular disease associated with the abnormality in a signal transduction pathway, various symptoms may be detected. Those skilled in the art recognize those symptoms that are associated with the various other diseases described herein.

Furthermore, since some adapter molecules recruit secondary signal transducer proteins towards the membrane, one measure of signal transduction is the concentration and localization of various proteins and complexes. In addition, conformational changes that are involved in the transmission of a signal may be observed using circular dichroism and fluorescence studies.

In preferred embodiments the screening method involves growing cells (i.e., in a dish) that either naturally or recombinantly express a G-coupled protein receptor, PYK2, and RAK. The test compound is added at a concentration from 0.1 uM to 100 uM and the mixture is incubated from 5 minutes to 2 hours. The ligand is added to the G-coupled protein receptor for preferably 5 to 30 minutes and the cells are lysed. RAK is isolated using immunoprecipitation or ELISA by binding to a specific monoclonal antibody. The amount of phosphorylation compared to cells that were not exposed to a test compound is measured using an anti-phosphotyrosine antibody (preferably polyclonal). Examples of compounds that could be tested in such screening methods include tyrphostins, quinazolines, quinoxolines, and quinolines.

The quinazolines, tyrphostins, quinolines, and quinoxolines referred to above include well known compounds such as those described in the literature. For example, representative publications describing quinazoline include Barker et al., EPO Publication No. 0 520 722 A1; Jones et al., U.S. Pat. No. 4,447,608; Kabbe et al., U.S. Pat. No. 4,757,072; Kaul and Vougioukas, U.S. Pat. No. 5,316,553; Kreighbaum and Comer, U.S. Pat. No. 4,343,940; Pegg and Wardleworth, EPO Publication No. 0 562 734 A1; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.* 37:2129–2131 (1994); Burke et al., *J. Med. Chem.* 36:425–432 (1993); and Burke et al. *BioOrganic Med. Chem. Letters* 2:1771–1774 (1992), all of which are incorporated by reference in their entirety, including any drawings.

Tyrphostins are described in Allen et al., *Clin. Exa. Immunol.* 91:141–156 (1993); Anafi et al., *Blood* 82:12:3524–3529 (1993); Baker et al., *J. Cell Sci.* 102:543–555 (1992); Bilder et al., *Amer. Physiol. Soc.* pp. 6363–6143:C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., "*J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992); Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888 (1992); Sauro and Thomas, *Life Sciences* 53:371–376 (1993); Sauro and Thomas, *J. Pharm. and Experimental Therapeutics* 267(3):119–1125 (1993); Wolbring et al., *J. Biol. Chem.* 269(36):22470–22472 (1994); and Yoneda et al., *Cancer Research* 51:4430–4435 (1991); all of which are incorporated herein by reference in their entirety, including any drawings.

In another aspect the invention features a method of diagnosis of an organism for a disease or condition characterized by an abnormality in a signal transduction pathway that contains an interaction between a PYK2 polypeptide and a NBP. The method involves detecting the level of interaction as an indication of said disease or condition.

By "organism" is meant any living creature. The term includes mammals, and specifically humans. Preferred organisms include mice, as the ability to treat or diagnose mice is often predictive of the ability to function in other organisms such as humans.

By "diagnosis" is meant any method of identifying a symptom normally associated with a given disease or condition. Thus, an initial diagnosis may be conclusively established as correct by the use of additional confirmatory evidence such as the presence of other symptoms. Current classification of various diseases and conditions is constantly changing as more is learned about the mechanisms causing the diseases or conditions. Thus, the detection of an important symptom, such as the detection of an abnormal level of interaction between PYK2 polypeptides and NBPs may form the basis to define and diagnose a newly named disease or condition. For example, conventional cancers are classified according to the presence of a particular set of symptoms. However, a subset of these symptoms may both be associated with an abnormality in a particular signalling pathway, such as the ras[21] pathway and in the future these diseases may be reclassified as ras[21] pathway diseases regardless of the particular symptoms observed.

Yet another aspect of the invention features a method for treatment of an organism having a disease or condition characterized by an abnormality in a signal transduction pathway. The signal transduction pathway contains an interaction between a PYK2 polypeptide and a NBP and the method involves promoting or disrupting the interaction, including methods that target the PYK2:NBP interaction directly, as well as methods that target other points along the pathway.

In preferred embodiments the signal transduction pathway regulates an ion channel, for example, a potassium ion, the disease or condition which is diagnosed or treated are those described above, the agent is a dominant negative mutant protein provided by gene therapy or other equivalent methods as described below and the agent is therapeutically effective and has an $EC_{50}$ or $IC_{50}$ as described below.

By "dominant negative mutant protein" is meant a mutant protein that interferes with the normal signal transduction pathway. The dominant negative mutant protein contains the domain of interest (e.g., an PYK2 polypeptide or a NBP), but has a mutation preventing proper signaling, for example by preventing binding of a second domain from the same protein. One example of a dominant negative protein is described in Millauer et al., *Nature* Feb. 10, 1994. The agent is preferably a peptide which blocks or promotes interaction of the PYK2 polypeptide and the NBP. The peptide may be recombinant, purified, or placed in a pharmaceutically acceptable carrier or diluent.

An $EC_{50}$ or $IC_{50}$ of less than or equal to 100 $\mu$M is preferable, and even more preferably less than or equal to 50 $\mu$M, and most preferably less that or equal to 20 $\mu$M. Such lower $EC_{50}$'s or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar potency and effectiveness. In addition, the molecule may have an $EC_{50}$ or $IC_{50}$ less than or equal to 100 $\mu$M at one or more, but not all cells chosen from the group consisting of parathyroid cell, bone osteoclast, juxtaglomerular kidney cell, proximal tubule kidney cell, distal tubule kidney cell, cell of the thick ascending limb of Henle's loop and/or collecting duct, central nervous system cell, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

By "therapeutically effective amount" is meant an amount of a pharmaceutical composition having a therapeutically relevant effect. A therapeutically relevant effect relieves to some extent one or more symptoms of the disease or condition in the patient; or returns to normal either partially or completely one or more physiological or biochemical parameters associated with or causative of the disease or condition. Generally, a therapeutically effective amount is between about 1 nmole and 1 $\mu$mole of the molecule, depending on its $EC_{50}$ or $IC_{50}$ and on the age and size of the patient, and the disease associated with the patient.

In other aspects, the invention provides transgenic, non-human mammals containing a transgene encoding a PYK2 polypeptide or a gene effecting the expression of a PYK2 polypeptide. Such transgenic nonhuman mammals are particularly useful as an in vivo test system for studying the effects of introducing a PYK2 polypeptide, regulating the expression of a PYK2 polypeptide (i.e., through the introduction of additional genes, antisense nucleic acids, or ribozymes).

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human PYK2 polypeptide. Native expression in an animal may be reduced by providing an amount of anti-sense RNA or DNA effective to reduce expression of the receptor.

In another aspect, the invention describes a polypeptide comprising a recombinant PYK2 polypeptide or a unique fragment thereof. By "unique fragment," is meant an amino acid sequence present in a full-length PYK2 polypeptide that is not present in any other naturally occurring polypeptide. Preferably, such a sequence comprises 6 contiguous amino acids present in the full sequence. More preferably, such a sequence comprises 12 contiguous amino acids present in the full sequence. Even more preferably, such a sequence comprises 18 contiguous amino acids present in the full sequence.

By "recombinant PYK2 polypeptide" is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

In another aspect, the invention describes a recombinant cell or tissue containing a purified nucleic acid coding for a PYK2 polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the PYK2 polypeptide.

In another aspect, the invention features a PYK2 polypeptide binding agent able to bind to a PYK2 polypeptide. The binding agent is preferably a purified antibody which recognizes an epitope present on a PYK2 polypeptide. Other binding agents include molecules which bind to the PYK2 polypeptide and analogous molecules which bind to a PYK2 polypeptide.

By "purified" in reference to an antibody is meant that the antibody is distinct from naturally occurring antibody, such as in a purified form. Preferably, the antibody is provided as a homogeneous preparation by standard techniques. Uses of antibodies to the cloned polypeptide include those to be used as therapeutics, or as diagnostic tools.

Other features and advantages of the invention will be apparent from the following description of the preferred embodiments thereof, and from the claims.

BRIEF DESCRIPTION OF THE FIGURES AND TABLES

FIG. 1 shows a schematic representation of the PYK2 domains (including a kinase domain, a proline rich domain, and a Fat domain) and potential binding sites (including YAEI, YLNV, and YVWV).

FIG. 2 shows a possible mechanism for the membrane depolarization and calcium influx that stimulate MEK and MAP kinase via activation of Ras. In PC12 cells, membrane depolarization leads to calcium influx through L-type calcium channels and activates MAP kinase. Calcium influx leads to activation of Ras and the activation of MAP in response to calcium influx is inhibited by a dominant negative mutant of Ras.

Table 1 shows the expression pattern and levels of PYK2 in various cell lines as checked by multiple methods.

DESCRIPTION OF THE PREFERRED EMBODIMENTS

Figure 1:
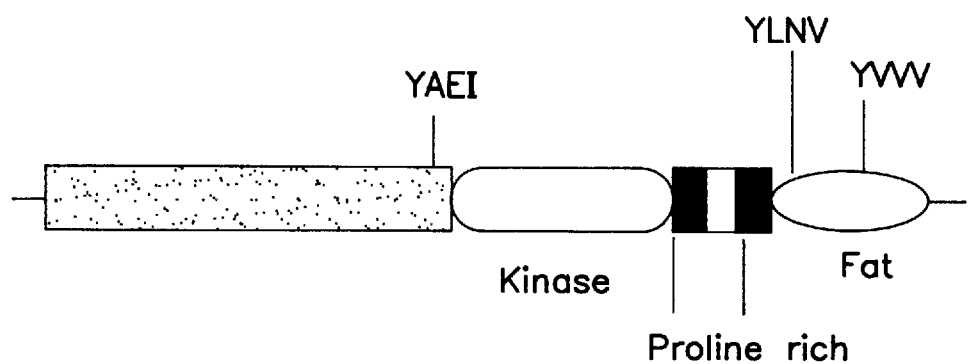
Figure 2:
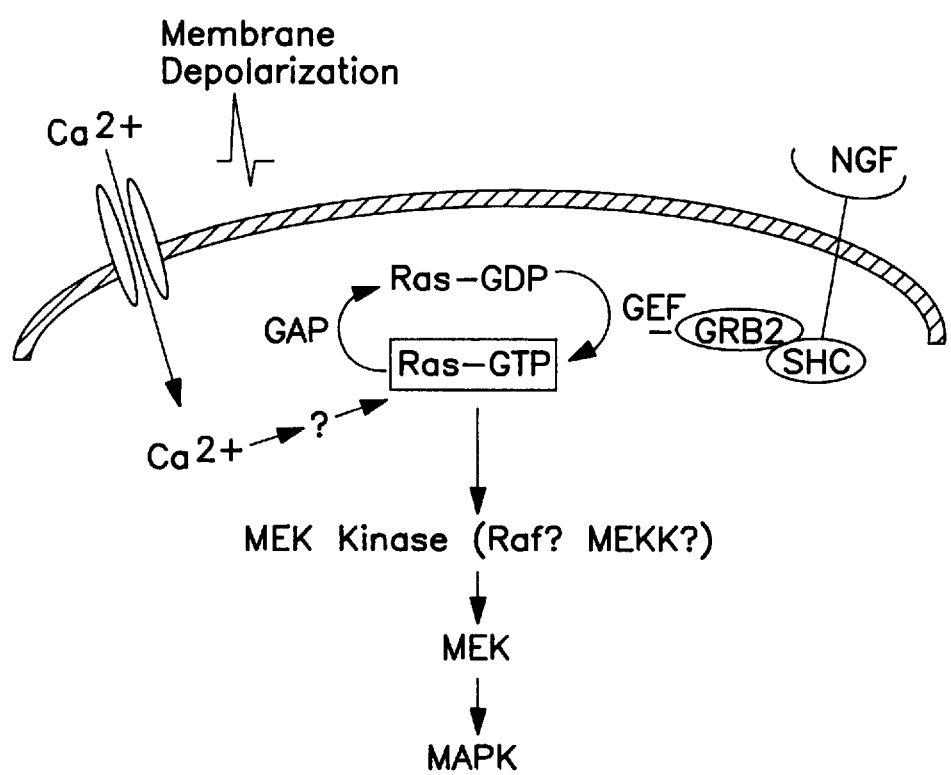

The present invention relates to PYK2 polypeptides, nucleic acids encoding such polypeptides, cells, tissues and animals containing such nucleic acids, antibodies to such polypeptides, assays utilizing such polypeptides, and methods relating to all of the foregoing. Those skilled in the art will recognize that many of the methods described below in relation to PYK-2, a NBP, or a complex of PYK-2 and a NBP could also be utilized with respect to the other members of this group.

I. Nucleic Acid Encoding A PYK2 Polypeptide.

Included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the PYK2 gene could be synthesized to give a nucleic acid sequence significantly different from that shown in SEQ ID NO: 2. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO: 2 or a derivative thereof. Any nucleotide or polynucleotide may be used in this regard, provided that its addition, deletion or substitution does not alter the amino acid sequence of SEQ ID NO:1 which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the PYK2 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

II. A Nucleic Acid Probe for the Detection of PYK2.

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. Molecular Cloning: A Laboratory Manual, second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, A Guide to Methods and Applications, edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. Molecular Cloning: A Laboratory Manual, second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

III. Probe Based Method And Kit For Detecting PYK2.

One method of detecting the presence of PYK2 in a sample comprises a) contacting said sample with the above-described nucleic acid probe, under conditions such that hybridization occurs, and b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of PYK2 in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

IV. DNA Constructs Comprising a PYK2 Nucleic Acid Molecule and Cells Containing These Constructs.

The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecule. The present invention also relates to a nucleic acid molecule comprising a transcriptional region functional in a cell, a sequence complimentary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule. The peptide may be purified from cells which have been altered to express the peptide. A cell is said to be "altered to express a desired peptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an PYK2 gene may be obtained by the above-described methods. This region may be retained for its transcriptional termination regulatory sequences, such as termination and polyadenylation. Thus, by retaining the 3'-region naturally contiguous to the DNA sequence encoding an PYK2 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an PYK2 sequence) are said to be operably linked if the nature of the linkage between the two DNA sequences does not (1) result in the introduction of a frame-shift mutation, (2) interfere with the ability of the promoter region sequence to direct the transcription of an PYK2 gene sequence, or (3) interfere with the ability of the an PYK2 gene sequence to be transcribed by the promoter region sequence. Thus, a promoter region would be operably linked to a DNA sequence if the promoter were capable of effecting transcription of that DNA sequence. Thus, to express an PYK2 gene, transcriptional and translational signals recognized by an appropriate host are necessary.

The present invention encompasses the expression of the PYK2 gene (or a functional derivative thereof) in either prokaryotic or eukaryotic cells. Prokaryotic hosts are, generally, very efficient and convenient for the production of recombinant proteins and are, therefore, one type of preferred expression system for the PYK2 gene. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coil*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express PYK2 (or a functional derivative thereof) in a prokaryotic cell, it is necessary to operably link the PYK2 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of E. coli, the α-amylase (Ulmanen et at., J. Bacteriol. 162:176–182 (1985)) and the ζ-28-specific promoters of B. subtilis (Gilman et at., Gene sequence 32:11–20(1984)), the promoters of the bacteriophages of Bacillus (Gryczan, In: The Molecular Biology of the Bacilli, Academic Press, Inc., New York (1982)), and Streptomyces promoters (Ward et at., Mol. Gen. Genet. 203:468–478(1986)). Prokaryotic promoters are reviewed by Glick (J. Ind. Microbiot. 1:277–282 (1987)); Cenatiempo (Biochimie 68:505–516(1986)); and Gottesman (Ann. Rev. Genet. 18:415–442 (1984)).

Proper expression in a prokaryotic cell also requires the presence of a ribosome binding site upstream of the gene sequence-encoding sequence. Such ribosome binding sites are disclosed, for example, by Gold et at. (Ann. Rev. Microbiol. 35:365–404(1981)). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the PYK2 peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, Science 240:1453–1459(1988). Alternatively, baculovirus vectors can be engineered to express large amounts of PYK2 in insects cells (Jasny, Science 238:1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of PYK2.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of PYK2 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gen. 1:273–288(1982)); the TK promoter of Herpes virus (McKnight, Cell 31:355–365 (1982)); the SV40 early promoter (Benoist et al., Nature (London) 290:304–310(1981)); the yeast gal4 gene sequence promoter (Johnston et al., Proc. Natl. Acad. Sci. (USA) 79:6971–6975(1982); Silver et al., Proc. Natl. Acad. Sci. (USA) 81:5951–5955 (1984)).

Translation of eukaryotic mRNA is initiated at the codon which encodes the first methionine. For this reason, it is preferable to ensure that the linkage between a eukaryotic promoter and a DNA sequence which encodes PYK2 (or a functional derivative thereof) does not contain any intervening codons which are capable of encoding a methionine (i.e., AUG). The presence of such codons results either in a formation of a fusion protein (if the AUG codon is in the same reading frame as the PYK2 coding sequence) or a frame-shift mutation (if the AUG codon is not in the same reading frame as the PYK2 coding sequence).

A PYK2 nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, Molec. Cell. Biol. 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. Coli* (such as, for example, pBR322, ColEl, pSC101, pACYC 184, πVX. Such plasmids are, for example, disclosed by Sambrook (cf. Molecular Cloning: A Laboratory Manual, second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacitli, Academic Press, New York (1982), pp. 307–329). Suitable Streptomyces plasmids include p1J101 (Kendall et al., J. Bacteriol. 169:4177–4183 (1987)), and streptomyces bacteriophages such as φC31 (Chater et al., In: Sixth International Symposium on Actinomycetales Biology, Akademiai Kaido, Budapest, Hungary (1986), pp. 45–54). Pseudomonas plasmids are reviewed by John et al. (Rev. Infect. Dis. 8:693–704(1986)), and Izaki (Jpn. J. Bacteriol. 33:729–742(1978)).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274(1982); Broach, In: The Molecular Biology of the Yeast Saccharomyces: Life Cycle and Inheritance, Cold Spring Harbor Laboratory, Cold Spring Harbor, N.Y., p. 445–470 (1981); Broach, Cell 28:203–204 (1982); Bollon et at., J. Ctin. Hematol. Oncol. 10:39–48 (1980); Maniatis, In: Cell Biology: A Comprehensive Treatise, Vol. 3, Gene Sequence Expression, Academic Press, New York, pp. 563–608(1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of PYK2 or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

V. Purified PYK2 Polypeptides.

A variety of methodologies known in the art can be utilized to obtain the peptide of the present invention. The peptide may be purified from tissues or cells which naturally produce the peptide. Alternatively, the above-described isolated nucleic acid fragments could be used to express the PYK2 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

VI. PYK2 Antibody And Hybridoma.

The present invention relates to an antibody having binding affinity to a PYK2 polypeptide. The polypeptide may have the amino acid sequence set forth in SEQ ID NO:1, or mutant or species variation thereof, or at least 9 contiguous amino acids thereof (preferably, at least 10, 15, 20, or 30 contiguous amino acids thereof).

The present invention also relates to an antibody having specific binding affinity to an PYK2 polypeptide. Such an antibody may be isolated by comparing its binding affinity to a PYK2 polypeptide with its binding affinity to another polypeptide. Those which bind selectively to PYK2 would be chosen for use in methods requiring a distinction between PYK2 and other polypeptides. Such methods could include, but should not be limited to, the analysis of altered PYK2 expression in tissue containing other polypeptides such as FAK.

The PYK2 proteins of the present invention can be used in a variety of procedures and methods, such as for the generation of antibodies, for use in identifying pharmaceutical compositions, and for studying DNA/protein interaction.

The PYK2 peptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., J. Immunol. Methods 35:1–21(1980)). Any animal (mouse, rabbit, and the like) which is known to produce antibodies can be immunized with the selected polypeptide.

Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124 (1988)). Hybridomas secreting the desired antibodies are cloned and the class and subclass is determined using procedures known in the art (Campbell, Monoclonal Antibody Technology: Laboratory Techniques in Biochemistry and Molecular Biology, supra (1984)).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., J. Histochem. Cytochem. 18:315(1970); Bayer et al., Meth. Enzym. 62:308(1979); Engval et al., Immunot. 109:129(1972); Goding, J. Immunol. Meth. 13:215(1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10(1986); Jacoby et al., Meth. Enzym. 34 Academic Press, New York (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, N.Y., pp. 289–307 (1992), and Kaspczak et al., Biochemistry 28:9230–8(1989).

Anti-peptide peptides can be generated by replacing the basic amino acid residues found in the PYK2 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VII. An Antibody Based Method And Kit For Detecting PYK2.

The present invention encompasses a method of detecting an PYK2 polypeptide in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample. Altered levels of PYK2 in a sample as compared to normal levels may indicate muscular disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is capable with the system utilized.

A kit contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody.

The compartmentalized kit may be as described above for nucleic acid probe kits. One skilled in the art will readily recognize that the antibodies described in the present invention can readily be incorporated into one of the established kit formats which are well known in the art.

VIII. Isolation of Compounds Which Interact With PYK2.

The present invention also relates to a method of detecting a compound capable of binding to a PYK2 polypeptide comprising incubating the compound with PYK2 and detecting the presence of the compound bound to PYK2. The compound may be present within a complex mixture, for example, serum, body fluid, or cell extracts.

The present invention also relates to a method of detecting an agonist or antagonist of PYK2 activity comprising incubating cells that produce PYK2 in the presence of a compound and detecting changes in the level of PYK2 activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing PYK2 associated activity in a mammal comprising administering to said mammal an agonist or antagonist to PYK2 in an amount sufficient to effect said agonism or antagonism. A method of treating diabetes mellitus, skeletal muscle diseases, Alzheimer's disease, or peripheral neuropathies in a mammal with an agonist or antagonist of PYK2 activity comprising administering the agonist or antagonist to a mammal in an amount sufficient to agonize or antagonize PYK2 associated functions is also encompassed in the present application.

IX. Transgenic Animals.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA* 82: 4438–4442 (1985) ) . Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, Experientia 47: 897–905 (1991). Other procedures for introduction of DNA into tissues of animals are described in U.S. Pat. No. , 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell* 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is cotransfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science* 244: 1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153–156 (1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel et al., *Science* 244:1281–1288 (1989); and Simms et al., *Bio/Technology* 6:179–183 (1988).

X. Compositions

The present invention relates to removing or reducing an abnormality in a signal transduction pathway, wherein the signal transduction pathway contains a PYK2 polypeptide. The present invention also relates to compositions and methods for the treatment of disorders which involve modulating the activity and/or level of individual components, and relates to methods for the identification of agents for such treatments. Additionally, the present invention relates to methods and compositions for prognostic evaluation of such disorders.

Described herein are compositions and methods for the prevention, prognostic evaluation, and treatment of disorders described herein, preferably cell proliferative disorders and hematopoietic cell disorders, in which a PYK2 polypeptide may be involved.

First, methods and compositions for the treatment of such disorders are described. Such methods and compositions may include, but are not limited to the agents capable of decreasing or inhibiting the interaction between a PYK2 polypeptide and a PYK2 polypeptide binding partner and agents capable of inhibiting or decreasing the activity of such complexes, agents capable of modulating the activity and/or level of individual components of the proteins, and the use and administration of such agents. Agents capable of modulating the activity and/or level of interaction between a PYK2 polypeptide and a PYK2 polypeptide binding partner include those agents that inhibit or decrease the dephosphorylating activity of tyrosine phosphatases.

Second, methods are described for the identification of such agents. These methods may include, for example, assays to identify agents capable of disrupting or inhibiting or promoting the interaction between components of the complexes (e.g., PYK2:NBP complexes), and may also include paradigms and strategies for the rational design of drugs capable of disruption and/or inhibition and/or promotion of such complexes.

The complexes involved in the invention include a PYK2 polypeptide and a NBP or derivatives thereof, as described below. Under standard physiological conditions, the components of such complexes are capable of forming stable, non-covalent attachments with one or more of the other complex components. Methods for the purification and production of such protein complexes, and of cells that exhibit such complexes are described below.

XI. Disruption of Protein Complexes

Disruption of complexes (e.g., PYK2:NBP complexes), for example by decreasing or inhibiting the interactions between component members of such a complex may have differing modulatory effects on the event involved, depending on the individual protein complex. "Disruption", as used here, is meant to refer not only to a physical separation of protein complex components, but also refers to a perturbation of the activity of the complexes, regardless of whether or not such complexes remain able, physically, to form. "Activity", as used here, refers to the function of the protein complex in the signal transduction cascade of the cell in which such a complex is formed, i.e., refers to the function of the complex in effecting or inhibiting a transduction of an extracellular signal into a cell. For example, the effect of complex disruption may augment, reduce, or block a signal normally transduced into the cell. Likewise, depending on the disorder involved, either augmentation, reduction, or blockage of a signal normally transduced into the cell will be desirable for the treatment of the disorder.

A disorder involving a complex may, for example, develop because the presence of such a complex brings about the aberrant inhibition of a normal signal transduction event. In such a case, the disruption of the complex would allow the restoration of the usual signal transduction event. Further, an aberrant complex may bring about an altered subcellular adapter protein localization, which may result in, for example, dysfunctional cellular events. An inhibition of the complex in this case would allow for restoration or maintenance of a normal cellular architecture. Still further, an agent or agents that cause(s) disruption of the complex may bring about the disruption of the interactions among other potential components of a complex.

Nucleotide sequences encoding peptide agents which are to be utilized intracellularly may be expressed in the cells of interest, using techniques which are well known to those of ordinary skill in the art. For example, expression vectors derived from viruses such as retroviruses, vaccinia virus, adenoviruses, adeno-associated virus, herpes viruses, or bovine papilloma virus, may be used for delivery and expression of such nucleotide sequences into the targeted cell population. Methods for the construction of such vectors are well known. See, for example, the techniques described in Maniatis et al., 1989, *Molecular Cloning: A Laboratory Manual*, Cold Spring Harbor Laboratory, N.Y. and in Ausubel et al., *Current Protocols in Molecular Biology*, Greene Publishing Associates and Wiley Interscience, N.Y. 1989. Complex-binding domains can be identified using, for example, techniques such as those described in Rotin et al. (Rotin et al., *EMBO J*. 11:559–567, 1992), Songyang et al. (Songyang et al., *Cell* 72:767–778, 1993), Felder et al., *Mol. Cell. Biol.* 13:1449–1455, 1993), Fantl et al. (*Cell* 69:413–422, 1992), and Domchek et al. (*Biochemistry* 31:9865–9870, 1992).

Alternatively, antibodies capable of interfering with complex formation may be produced as described below and administered for the treatment of disorders involving a component capable of forming a complex with another protein. Alternatively, nucleotide sequences encoding single-chain antibodies may be expressed within the target cell population by utilizing, for example, techniques such as those described in Marasco et al. (Marasco et al., *Proc. Natl. Acad. Sci. USA* 90:7889–7893, 1993). Agents which act intracellularly to interfere with the formation and/or activity of the protein complexes of the invention may also be small organic or inorganic compounds. A method for identifying these and other intracellular agents is described below.

XII. Antibodies to Complexes

Described herein are methods for the production of antibodies which are capable of specifically recognizing a complex or an epitope thereof, or of specifically recognizing an epitope on either of the components of the complex, especially those epitopes which would not be recognized by the antibody when the component is present separate and apart from the complex. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of a complex in a biological sample, or, alternatively, as a method for the inhibition of a complex formation, thus inhibiting the development of a disorder.

Polyclonal antibodies are heterogeneous populations of antibody molecules derived from the sera of animals immunized with an antigen, such as a complex, or an antigenic functional derivative thereof. For the production of polyclonal antibodies, various host animals may be immunized by injection with the complex including but not limited to rabbits, mice, rats, etc. Various adjuvants may be used to increase the immunological response, depending on the host species, including but not limited to Freund's (complete and incomplete), mineral gels such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

A monoclonal antibody, which is a substantially homogeneous population of antibodies to a particular antigen, may be obtained by any technique which provides for the production of antibody molecules by continuous cell lines in culture. These include, but are not limited to the hybridoma technique of Kohler and Milstein (*Nature* 256:495–497, 1975) and U.S. Pat. No. 4,376,110), the human B-cell hybridoma technique (Kosbor et al., *Immunology Today* 4:72, 1983; Cole et al., *Proc. Natl. Acad. Sci. USA* 80:2026–2030, 1983), and the EBV-hybridoma technique (Cole et al., *Monoclonal Antibodies And Cancer Therapy*, Alan R. Liss, Inc,.1985, pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Natl. Acad. Sci.*, 81:6851–6855, 1984; Neuberger et al., *Nature*, 312:604–608, 1984; Takeda et al., *Nature*, 314:452–454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. 4,946,778; Bird, *Science* 242:423–426, 1988; Huston et al., *Proc. Natl. Acad. Sci. USA* 85:5879–5883, 1988; and Ward et al., *Nature* 334:544–546, 1989) can be adapted to produce complex-specific single chain antibodies. Single chain antibodies are formed by linking the heavy and light chain fragment of the Fv region via an amino acid bridge, resulting in a single chain polypeptide.

Antibody fragments which contain specific binding sites of a complex may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity to the PTK/adapter complex.

One or more components of a protein complex may be present at a higher than normal cellular level (i.e., higher than the concentration known to usually be present in the cell type exhibiting the protein complex of interest and/or may exhibit an abnormally increased level of cellular activity (i.e., greater than the activity known to usually be present in the cell type exhibiting the protein complex of interest).

For example, the gene encoding a protein complex component may begin to be overexpressed, or may be amplified (i.e., its gene copy number may be increased) in certain cells, leading to an increased number of component molecules within these cells. Additionally, a gene encoding a protein complex component may begin to express a modified protein product that exhibits a greater than normal level of activity. "Activity", here, refers to the normal cellular function of the component, either enzymatic or structural whose function may include, for example, bringing two or more cellular molecules into the appropriate proximity.

Such an increase in the cellular level and/or activity of a protein complex may lead to the development of a disorder. Treatment of such disorders may, therefore, be effectuated by the administration of agents which decrease the cellular level and/or the activity of the overexpressed and/or overactive protein complex component. Techniques for decreasing the cellular level and/or the activity of one or more of the protein complex components of interest may include, but are not limited to antisense or ribozyme approaches, and/or gene therapy approaches, each of which is well known to those of skill in the art.

XIII. Antisense and Ribozyme Approaches

Included in the scope of the invention are oligoribonucleotides, including antisense RNA and DNA molecules and ribozymes that function to inhibit translation of one or more components of a protein complex. Anti-sense RNA and DNA molecules act to directly block the translation of mRNA by binding to targeted mRNA and preventing protein translation. With respect to antisense DNA, oligodeoxyribonucleotides derived from the translation initiation site, e.g., between −10 and +10 regions of the relevant nucleotide sequence, are preferred.

Ribozymes are enzymatic RNA molecules capable of catalyzing the specific cleavage of RNA. The mechanism of ribozyme action involves sequence specific interaction of the ribozyme molecule to complementary target RNA, followed by a endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, Draper PCT WO 93/23569.

Both anti-sense RNA and DNA molecules and ribozymes of the invention may be prepared by any method known in the art for the synthesis of RNA molecules. See, Draper, id. hereby incorporated by reference herein. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

XIV. Gene Therapy

PYK2 or its genetic sequences will also be useful in gene therapy (reviewed in Miller, *Nature* 357:455–460, (1992). Miller states that advances have resulted in practical approaches to human gene therapy that have demonstrated positive initial results. An in vivo model of gene therapy for human severe combined immunodeficiency is described in Ferrari, et al., *Science* 251:1363–1366, (1991). The basic science of gene therapy is described in Mulligan, *Science* 260:926–931, (1993).

In one preferred embodiment, an expression vector containing the PYK2 coding sequence is inserted into cells, the cells are grown in vitro and then infused in large numbers into patients. In another preferred embodiment, a DNA segment containing a promoter of choice (for example a strong promoter) is transferred into cells containing an endogenous PYK2 in such a manner that the promoter segment enhances expression of the endogenous PYK2 gene (for example, the promoter segment is transferred to the cell such that it becomes directly linked to the endogenous PYK2 gene).

The gene therapy may involve the use of an adenovirus containing PYK2 cDNA targeted to a tumor, systemic PYK2 increase by implantation of engineered cells, injection with PYK2 virus, or injection of naked PYK2 DNA into appropriate tissues.

Target cell populations (e.g., hematopoietic or nerve cells) may be modified by introducing altered forms of PYK2 in order to modulate the activity of such cells. For example, by reducing or inhibiting an a nerve cell within target cells, an abnormal response leading to a condition may be decreased, inhibited, or reversed. Deletion or missense mutants of PYK2, that retain the ability to interact with other components of the nervous system but cannot participate in normal function may be used to inhibit an abnormal, deleterious response.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant PYK2 protein into the targeted cell population (e.g., tumor cells). Methods which are well known to those skilled in the art can be used to construct recombinant viral vectors containing coding sequences. See, for example, the techniques described in Maniatis et al., *Molecular Cloning: A Laboratory Manual*, Cold Spring Harbor Laboratory, N.Y. (1989), and in Ausubel et al., *Current Protocols in Molecular Biology*, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi MR, *Cell* 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745–52 (1987)); electroporation, wherein cells are exposed to large voltage pulses to introduce holes into the membrane (Chu G. et al., *Nucleic Acids Res.*, 15:1311–26 (1987)); lipofection/liposome fusion, wherein DNA is packaged into lipophilic vesicles which fuse with a target cell (Felgner PL., et al., *Proc. Natl. Acad. Sci. USA*. 84:7413–7 (1987)); and particle bombardment using DNA bound to small projectiles (Yang NS. et al., *Proc. Natl. Acad. Sci.* 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel DT et al., *Am. J. Respir. Cell. Mol. Biol.*, 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding PYK2 is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

XV. Pharmaceutical Formulations and Modes of Administration

The particular compound, antibody, antisense or ribozyme molecule that affects the protein complexes and the disorder of interest can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics*, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity) The magnitude of an administered dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Some methods of delivery that may be used include:

a. encapsulation in liposomes, b. transduction by retroviral vectors, c. localization to nuclear compartment utilizing nuclear targeting site found on most nuclear proteins, d. transfection of cells ex vivo with subsequent reimplantation or administration of the transfected cells, e. a DNA transporter system.

A PYK2 nucleic acid sequence may be administered utilizing an ex vivo approach whereby cells are removed from an animal, transduced with the PYK2 nucleic acid sequence and reimplanted into the animal. The liver can be accessed by an ex vivo approach by removing hepatocytes from an animal, transducing the hepatocytes in vitro with the PYK2 nucleic acid sequence and reimplanting them into the animal (e.g., as described for rabbits by Chowdhury et al, *Science* 254: 1802–1805, 1991, or in humans by Wilson, *Hum. Gene Ther.* 3: 179–222, 1992) incorporated herein by reference.

Many nonviral techniques for the delivery of a PYK2 nucleic acid sequence into a cell can be used, including direct naked DNA uptake (e.g., Wolff et al., *Science* 247: 1465–1468, 1990), receptor-mediated DNA uptake, e.g., using DNA coupled to asialoorosomucoid which is taken up by the asialoglycoprotein receptor in the liver (Wu and Wu, *J. Biol. Chem.* 262: 4429–4432, 1987; Wu et al., *J. Biol. Chem.* 266: 14338–14342, 1991), and liposome-mediated delivery (e.g., Kaneda et al., *Expt. Cell Res.* 173: 56–69, 1987; Kaneda et al., *Science* 243: 375–378, 1989; Zhu et al., *Science* 261: 209–211, 1993). Many of these physical methods can be combined with one another and with viral techniques; enhancement of receptor-mediated DNA uptake can be effected, for example, by combining its use with adenovirus (Curiel et al., *Proc. Natl. Acad. Sci. USA* 88: 8850–8854, 1991; Cristiano et al., *Proc. Natl. Acad. Sci. USA* 90: 2122–2126, 1993).

The PYK2 or nucleic acid encoding PYK2 may also be administered via an implanted device that provides a support for growing cells. Thus, the cells may remain in the implanted device and still provide the useful and therapeutic agents of the present invention.

XVI. Identification of Agents

The complexes, components of such complexes, functional equivalents thereof, and/or cell lines that express such components and exhibit such protein complexes may be used to screen for additional compounds, antibodies, or other molecules capable of modulating the signal transduction event such complexes are involved in. Methods for purifying and/or producing such complexes, components of the complexes, functional equivalents thereof, and/or cell lines are described herein. The compounds, antibodies, or other molecules identified may, for example, act to disrupt the protein complexes of the invention (i.e., decrease or inhibit interactions between component members of the complexes, thereby causing physical separation of the components, and/or perturbing the activity of the complexes) or may lower the cellular level and/or decrease the activity of one or more of the components of such complexes.

Such compounds may include, but are not limited to, peptides made of D- and/or L-configuration amino acids (in, for example, the form of random peptide libraries; see Lam et al., *Nature* 354:82–84, 1991), phosphopeptides (in, for example, the form of random or partially degenerate, directed phosphopeptide libraries, see Songyang et al., *Cell* 767–778, 1993), antibodies, and small organic or inorganic molecules. Synthetic compounds, natural products, and other sources of potentially biologically active materials may be screened in a variety of ways, as described herein. The compounds, antibodies, or other molecules identified may be used as oncogenic disorder treatments, as described herein.

Compounds that bind to individual components, or functional portions of the individual components of the complexes (and may additionally be capable of disrupting complex formation) may be identified.

One such method included within the scope of the invention is a method for identifying an agent to be tested for an ability to modulate a signal transduction pathway disorder. The method involves exposing at least one agent to a protein comprising a functional portion of a member of the protein complex for a time sufficient to allow binding of the agent to the functional portion of the member; removing nonbound agents; and determining the presence of the compound bound to the functional portion of the member of the protein complex, thereby identifying an agent to be tested for an ability to modulate a disorder involving a polypeptide complex.

By "signal transduction disorder" is meant any disease or condition associated with an abnormality in a signal transduction pathway. The protein complex referred to below is a physical association of dynamin and a PYK2 polypeptide. The level of interaction between the two components of the complex may be abnormal and thus cause the abnormality in the signal transduction pathway. Alternatively, the level of interaction between the complex components may be normal, but affecting that interaction may effectively treat a signal transduction pathway disorder.

The term "protein" refers to a compound formed of 5–50 or more amino acids joined together by peptide bonds. An "amino acid" is a subunit that is polymerized to form proteins and there are twenty amino acids that are universally found in proteins. The general formula for an amino acid is $H_2N$—CHR—COOH, in which the R group can be anything from a hydrogen atom (as in the amino acid glycine) to a complex ring (as in the amino acid tryptophan).

A functional portion of an individual component of the complexes may be defined here as a protein portion of an individual component of a complex still capable of forming a stable complex with another member of the complex under standard cellular and physiological conditions. For example, a functional portion of a component may include, but is not limited to, a protein portion of dynamin which is still capable of stably binding a corresponding PYK2 polypeptide of an associated protein, and thus is still capable of forming a complex with that protein. Further, in the case of the catalytic domains of the individual components of the invention, a functional portion of a catalytic domain may refer to a protein still capable of stably binding a substrate molecule under standard physiological conditions.

One method utilizing this approach that may be pursued in the isolation of such complex component-binding molecules would include the attachment of a component molecule, or a functional portion thereof, to a solid matrix, such as agarose or plastic beads, microtiter wells, petri dishes, or membranes composed of, for example, nylon or nitrocellulose, and the subsequent incubation of the attached component molecule in the presence of a potential component-binding compound or compounds. Attachment to said solid support may be direct or by means of a component specific antibody bound directly to the solid support. After incubation, unbound compounds are washed away, component-bound compounds are recovered. By utilizing this procedure, large numbers of types of molecules may be simultaneously screened for complex component-binding activity.

The complex components which may be utilized in the above screening method may include, but are not limited to, molecules or functional portions thereof, such as catalytic domains, phosphorylation domains, extracellular domains, or portions of extracellular domains, such as ligand-binding domains, and adaptor proteins, or functional portions thereof. The peptides used may be phosphorylated, e.g., may contain at least one phosphorylated amino acid residue, preferably a phosphorylated Tyr amino acid residue, or may be unphosphorylated. A phosphorylation domain may be defined as a peptide region that is specifically phosphorylated at certain amino acid residues. A functional portion of such a phosphorylation domain may be defined as a peptide capable of being specifically phosphorylated at certain amino acids by a specific protein.

Molecules exhibiting binding activity may be further screened for an ability to disrupt protein complexes. Alternatively, molecules may be directly screened for an ability to promote the complexes. For example, in vitro complex formation may be assayed by, first, immobilizing one component, or a functional portion thereof, of the complex of interest to a solid support. Second, the immobilized complex component may be exposed to a compound such as one identified as above, and to the second component, or a functional portion thereof, of the complex of interest. Third, it may be determined whether or not the second component is still capable of forming a complex with the immobilized component in the presence of the compound. In addition, one could look for an increase in binding.

Additionally, complex formation in a whole cell may be assayed by utilizing co-immunoprecipitation techniques well known to those of skill in the art. Briefly, a cell line capable of forming a complex of interest may be exposed to a compound such as one identified as above, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

A preferred method for assessing modulation of complex formation within a cell utilizes a method similar to that described above. Briefly, a cell line capable of forming a complex of interest is exposed to a test compound. The cells are lysed and the lysate contacted with an antibody specific to one component of the complex, said antibody having been previously bound to a solid support. Unbound material is washed away, and the bound material is exposed to a second antibody, said second antibody binding specifically to a second component of the complex. The amount of second antibody bound is easily detected by techniques well known in the art. Cells exposed to an inhibitory test compound will have formed a lesser amount of complex compared to cells not exposed to the test compound, as measured by the amount of second antibody bound. Cells exposed to a test compound that promotes complex formation will have an increased amount of second antibody bound.

The effect of an agent on the differentiation capability of the complex of interest may be directly assayed. Such agents may, but are not required to, include those agents identified by utilizing the above screening technique. For example, an agent or agents may be administered to a cell such as a neuronal cell, capable of forming a complex, for example, which, in the absence of any agent, would not lead to the cell's differentiation. The differentiation state of the cell may then be measured either in vitro or in vivo. One method of measurement may involve observing the amount of neurile growth present.

Agents capable of disrupting complex formation and capable of reducing or inhibiting disorders, which involve the formation of such complexes, or which involve the lack of formation of such complexes, may be used in the treatment of patients exhibiting or at risk for such disorders. A sufficient amount of agent or agents such as those described above may be administered to a patient so that the symptoms of the disease or condition are reduced or eliminated.

XVII. Purification and Production of Complexes

Described in this Section are methods for the synthesis or recombinant expression of components, or fragments thereof, of the protein complexes of the invention. Also described herein are methods by which cells exhibiting the protein complexes of the invention may be engineered.

The complexes of the invention may be substantially purified, i.e., may be purified away from at least 90% (on a weight basis), and from at least 99%, if desired, of other proteins, glycoproteins, and other macromolecules with which it is associated. Such purification can be achieved by utilizing a variety of procedures well known to those of skill in the art, such as subjecting cells, tissue or fluid containing the complex to a combination of standard methods, for example, ammonium sulfate precipitation, molecular sieve chromatography, and/or ion exchange chromatography.

Alternatively, or additionally, a complex may be purified by immunoaffinity chromatography using an immunoabsorbent column to which an antibody is immobilized which is capable of binding to one or more components of the complex. Such an antibody may be monoclonal or polyclonal in origin. Other useful types of affinity purification for the protein complex may utilize, for example, a solid-phase substrate which binds the catalytic kinase domain of a protein, or an immobilized binding site for noncatalytic domains of the components of the complex, which bind in such a manner as to not disrupt the complex. The complex of the present invention may be biochemically purified from a variety of cell or tissue sources.

Methods for the synthesis of polypeptides or fragments thereof, which are capable of acting as components of the complexes of the present invention, are well-known to those of ordinary skill in the art. See, for example, Creighton, *Proteins: Structures and Molecular Principles*, W. H. Freeman and Co., N.Y. (1983), which is incorporated herein, by reference, in its entirety.

Components of a complex which have been separately synthesized or recombinantly produced, may be reconstituted to form a complex by standard biochemical techniques well known to those skilled in the art. For example, samples containing the components of the complex may be combined in a solution buffered with greater than about 150 mM NaCl, at a physiological pH in the range of 7, at room temperature. For example, a buffer comprising 20 mM Tris-HCl, pH 7.4, 137 mM NaCl, 10% glycerol, 1% Triton X-100, 0.1% SDS, 0.5% deoxycholate and 2 mM EDTA could be used.

Methods for preparing the components of complexes of the invention by expressing nucleic acid encoding proteins are described herein. Methods which are well known to those skilled in the art can be used to construct expression vectors containing protein coding sequences and appropriate transcriptional and translational control signals. These methods include, for example, in vitro recombinant DNA techniques, synthetic techniques and in vivo recombination/genetic recombination. DNA and RNA synthesis may, additionally, be performed using an automated synthesizers. See, for example, the techniques described in Maniatis et al., *Molecular Cloning: A Laboratory Manual*, Cold Spring Harbor Laboratory, N.Y. (1989), and in Ausubel et al., *Current Protocols in Molecular Biology*, Greene Publishing Associates and Wiley Interscience, N.Y. (1989).

A variety of host-expression vector systems may be utilized to express the coding sequences of the components of the complexes of the invention. Such host-expression systems represent vehicles by which the coding sequences of interest may be produced, but also represent cells which may, when transformed or transfected with the appropriate nucleotide coding sequences, exhibit the protein complexes of the invention. These include but are not limited to microorganisms such as bacteria (e.g., *E. coli, B. subtilis*) transformed with recombinant bacteriophage DNA, plasmid DNA or cosmid DNA expression vectors containing protein coding sequences; yeast (e.g., Saccharomyces and Pichia) transformed with recombinant yeast expression vectors containing the protein coding sequencers; insect cell systems infected with recombinant virus expression vectors (e.g., baculovirus) containing the protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter)

In bacterial systems a number of expression vectors may be advantageously selected depending upon the use intended for the complex being expressed. For example, when large quantities of complex proteins are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., *EMBO J*. 2:1791, 1983), in which the protein coding sequence may be ligated individually into the vector in frame with the lac Z coding region so that a fusion protein is produced; pIN vectors (Inouye and Inouye, *Nucleic acids Res*. 13:3101–3109, 1985; Van Heeke & Schuster, *J. Biol. Chem*. 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned protein can be released from the GST moiety.

In an insect system, Autographa californica nuclear polyhidrosis virus (AcNPV) is used as a vector to express foreign genes. The virus grows in Spodoptera frugiperda cells. The complex coding sequence may be cloned individually into non-essential regions (for example the polyhedrin gene) of the virus and placed under control of an AcNPV promoter (for example the polyhedrin promoter). Successful insertion of the PTK/adaptor complex coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., *J. Biol*. 46:584, 1983; Smith, U.S. Pat. No. 4,215,051).

In mammalian host cells, a number of viral based expression systems may be utilized. In cases where an adenovirus is used as an expression vector, the complex coding sequence may be ligated to an adenovirus transcription/translation control complex, e.g., the late promoter and tripartite leader sequence. This chimeric gene may then be inserted in the adenovirus genome by in vitro or in vivo recombination. Insertion into a non-essential region of the viral genome (e.g., region E1 or E3) will result in a recombinant virus that is viable and capable of expressing proteins in infected hosts. (E.g., See Logan & Shenk, *Proc. Natl. Acad. Sci. USA* 81:3655–3659, 1984) Specific initiation signals may also be required for efficient translation of inserted coding sequences. These signals include the ATG initiation codon and adjacent sequences.

In cases where an entire protein gene, including its own initiation codon and adjacent sequences, is inserted into the appropriate expression vector, no additional translational control signals may be needed. However, in cases where only a portion of the coding sequence is inserted, exogenous translational control signals, including the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in *Enzymol*. 153:516–544, 1987)

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably coexpress both the proteins may be engineered. Rather than using expression vectors which contain viral origins of replication, host cells can be transformed with the protein encoding DNA independently or coordinately controlled by appropriate expression control elements (e.g., promoter, enhancer, sequences, transcription terminators, polyadenylation sites, etc.), and a selectable marker.

Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which coexpress both the PTK and adaptor protein. Such engineered cell lines are particularly useful in screening and evaluation of compounds that effect signals mediated by the complexes.

A number of selection systems may be used, including but not limited to the herpes simplex virus thymidine kinase (Wigler et al., *Cell* 11:223, 1977), hypoxanthine-guanine phosphoribosyltransferase (Szybalska & Szybalski, *Proc. Natl. Acad. Sci. USA* 48:2026, 1962), and adenine phosphoribosyltransferase (Lowy et al., *Cell* 22:817, 1980) genes can be employed in tk⁻, hgprt⁻ or aprt⁻ cells, respectively. Also, antimetabolite resistance can be used as the basis of selection for dhfr, which confers resistance to methotrexate (Wigler et al., *Natl. Acad. Sci. USA* 77:3567, 1980; O'Hare et al., *Proc. Natl. Acad. Sci. USA* 78:1527, 1981); gpt, which confers resistance to mycophenolic acid (Mulligan & Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al. *Gene* 30:147, 1984) genes.

New members of the protein families capable of forming the complexes of the invention may be identified and isolated by molecular biological techniques well known in the art. For example, a previously unknown protein encoding gene may be isolated by performing a polymerase chain reaction (PCR) using two degenerate oligonucleotide primer pools designed on the basis of highly conserved sequences within domains common to members of the protein family. The template for the reaction may be cDNA obtained by reverse transcription of mRNA prepared from cell lines or tissue known to express complexes. The PCR product may be subcloned and sequenced to insure that the amplified sequences represent the sequences of a member of the PTK or adaptor subfamily. The PCR fragment may then be used to isolate a full length protein cDNA clone by radioactively labeling the amplified fragment and screening a bacteriophage cDNA library. Alternatively, the labeled fragment may be used to screen a genomic library. For a review of cloning strategies which may be used. See e.g., Maniatis, *Molecular Cloning: A Laboratory Manual*, Cold Springs Harbor Press, N.Y. (1989); and Ausubel et al., *Current Protocols in Molecular Biology*, Green Publishing Associates and Wiley Interscience, N.Y. (1989). A general method for cloning previously unknown proteins has been described by Skolnik (Skolnik, E. Y., *Cell* 65:75, 1991) and Skolnik et al., (U.S. patent application Ser. No. 07/643,237) which are incorporated herein, by reference, in their entirety, including drawings.

XVIII. Derivatives of Complexes

Also provided herein are functional derivatives of a complex. By "functional derivative" is meant a "chemical derivative," "fragment," "variant," "chimera," or "hybrid" of the complex, which terms are defined below. A functional derivative retains at least a portion of the function of the protein, for example reactivity with an antibody specific for the complex, enzymatic activity or binding activity mediated through noncatalytic domains, which permits its utility in accordance with the present invention.

A "chemical derivative" of the complex contains additional chemical moieties not normally a part of the protein. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in Remington's Pharmaceutical Sciences (1980). Procedures for coupling such moieties to a molecule are well known in the art. Covalent modifications of the protein complex or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing primary amine containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N═C═N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the complexes to each other or the complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[p-azidophenyl) dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W. H. Freeman & Co., San Francisco, pp. 79–86 (1983)), acetylation of the Nterminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in *Remington's Pharmaceutical Sciences*, 18th ed., Mack Publishing Co., Easton, Pa. (1990).

The term "fragment" is used to indicate a polypeptide derived from the amino acid sequence of the proteins, of the complexes having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence. Fragments of a protein, when present in a complex resembling the naturally occurring complex, are useful for screening for compounds that act to modulate signal transduction, as described below. It is understood that such fragments, when present in a complex may retain one or more characterizing portions of the native complex. Examples of such retained characteristics include: catalytic activity; substrate specificity; interaction with other molecules in the intact cell; regulatory functions; or binding with an antibody specific for the native complex, or an epitope thereof.

Another functional derivative intended to be within the scope of the present invention is a complex comprising at least one "variant" polypeptide which either lack one or more amino acids or contain additional or substituted amino acids relative to the native polypeptide. The variant may be derived from a naturally occurring complex component by appropriately modifying the protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native complex, as described above.

A functional derivative of complexes comprising proteins with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, DNA 2:183) wherein nucleotides in the DNA coding the sequence are modified such that a modified coding sequence is modified, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art. The functional derivatives of the complexes typically exhibit the same qualitative biological activity as the native complexes.

XIX. Evaluation of Disorders

The protein complexes of the invention involved in disorders may be utilized in developing a prognostic evaluation of the condition of a patient suspected of exhibiting such a disorder. For example, biological samples obtained from patients suspected of exhibiting a disorder involving a protein complex may be assayed for the presence of such complexes. If such a protein complex is normally present, and the development of the disorder is caused by an abnormal quantity of the complex, the assay should compare complex levels in the biological sample to the range expected in normal tissue of the same cell type.

Among the assays which may be undertaken may include, but are not limited to isolation of the protein complex of interest from the biological sample, or assaying for the presence of the complex by exposing the sample to an antibody specific for the complex, but non-reactive to any single, non-complexed component, and detecting whether antibody has specifically bound.

Alternatively, one or more of the components of the protein complex may be present in an abnormal level or in a modified form, relative to the level or form expected is normal, nononcogenic tissue of the same cell type. It is possible that overexpression of both components may indicate a particularly aggressive disorder. Thus, an assessment of the individual and levels of mRNA and protein in diseased tissue cells may provide valuable clues as to the course of action to be undertaken in treatment of such a disorder. Assays of this type are well known to those of skill in the art, and may include, but are not limited to, Northern blot analysis, RNAse protection assays, and PCR for determining mRNA levels. Assays determining protein levels are also well known to those of skill in the art, and may include, but are not limited to, Western blot analysis, immunoprecipitation, and ELISA analysis. Each of these techniques may also reveal potential differences in the form (e.g., the primary, secondary, or tertiary amino acid sequence, and/or post-translational modifications of the sequence) of the component(s).

EXAMPLES

The examples below are non-limiting and are merely representative of various aspects and features of the procedures used to identify the full-length nucleic and amino acid sequences of PYK-2.

Materials and Methods

Chemicals

Bradykinin, pertusis toxin, cholera toxin, forskolin, phorbol 12-myristate 13-acetate (PMA), calcium ionophore A23187, carbachol, muscarine, atrophine, mecamylamine, and 1,1-dimethyl-4-phenyl piperazinium iodide (DMPP) were purchased from Sigma.

Cloning of PYK2 cDNA

RNA from rat spinal cord was used to prepare cDNA utilizing the reverse transcriptase of Molony murine leukemia virus ($^{BRL}$) according to the manufacturer's protocol. The cDNA was amplified by PCR utilizing degenerate oligonucleotides primers corresponding to conserved tyrosine kinase motifs from subdomains TK6 and TK9 of PYK1; (the sense and antisense primers correspond to amino acid sequences IHRDLAARN [SEQ ID NO 3] and WMF-GVTLW [SEQ ID NO 4] respectively). The PCR was carried out under the following conditions; 1 min at 94° C.; 1 min at 50° C. and 1 min at 68° C. for 35 cycles. PCR products were electrophoresed, checked by the size (~210bp), purified and subcloned into pBluescript (Stratagene). Novel clones were screened by DNA sequencing. The cDNA insert of clone #38 was used as probe to screen human brain cDNA libraries (human fetal brain λgt 10 and human brain λgt 11, 6×10$^5$ recombinant clones each) essentially as described by Maniatis ().

DNA Sequencing and analysis

DNA sequencing was performed on both strands utilizing series of oligonucleotide primers and subclones. The nucleotide sequence and the deduced amino acid sequence were subjected to homology search with Genbank and PIR databases using FASTA and BLAST mail-server program.

Northern blot analysis

Total RNA was isolated from mouse tissues by the acid guanidinium thicynate-phenol-chloroform method (Anal. Biochem. 162; 156, 1987). Poly (A)$^+$ RNA was denaturated with formaldehyde and electrophoresed on a 1% agarose/ 0.7% formaldehyde gel. RNAs were transferred to a nitrocellulose membrane and hybridized with $^{32}$p-labeled probe that contained the cDNA insert of clone #38 as described above.

Antibodies

Antibodies against PYK2 were raised in rabbits immunized (HTl) either by GST fusion protein containing residues 362–647 or PYK2 or by synthetic peptide corresponding to the 15 amino acids at the N-terminal end of PYK2. Antisera were checked by immunoprecipitation and immunoblot analysis, and the specificity was confirmed either by reactivity to the related protein Fak or by competition with the antigenic or control peptides.

Cells and cell culture

PC12-rat pheochromocytoma cells were cultured in Dulbecco's modified Eagle's medium containing 10% horse serum, 5% fetal bovine serum, 10 μg/ml streptomycin and 100 units of penicillin/ml. NIH3T3, 293, GP+E-86 and PA317 cells were grown in Dulbecco's modified Eagle's medium containing 10% fetal bovine serum, 100 μg/ml streptomycin and 100 units of penicillin/ml.

Transfections and infections

For stable expression in PC12 cells, PYK2 was subcloned into the retroviral vector pLXSN (Miller and Rosman, Biotechniques 7:980, 1989). The construct was used to transfect GP+E-86 cells using lipofectimine reagent (GIBCO BRL). 48 hours after transfection, virus containing supernatants were collected. Pure retrovirus-containing cell-free supernatant were added to PC12 cells in the presence of polybrene (8 μg/ml, Aldrich) for 4 hours (MCB 12 491, 1992). After 24 hours, infected PC12 cells were split into growing medium containing 350 μl/mg G418. G418 resistant colonies were isolated two to three weeks later and the level of expression was determined by western blot analysis.

Stable cell lines of NIH3T3 that overexpress PYK2 were established by contransfection of PYK2 subcloned into pLSV together with pSV2neo utilizing lipofectamine reagent (GIBCO BRL). Following transfection the cells were grown in Dulbecco's modified Eagle's medium containing 10% fetal bovine serum and 1 mg/ml G418. Transient transfections into 293 cells were performed by using the calcium phosphate technique (*).

Constructs

GST-PYK2— a DNA fragment of λ900 bp corresponding to residues 362–647 of PYK2 was amplified by PCR utilizing the following oligonucleotide primers: 5'-CGGGATCCTCATCATCCATCCTAGGAAAGA-3' (sense) [SEQ ID NO 5] and 5'-CGGGAATTCGTC GTAGTCCCAGCAGCGGGT-3' (antisense) [SEQ ID NO 6].

The PCR product was digested with HamHI and ECORI and subcloned into pGEX3X (Pharmacia). Expression of GST-PYK2 fusion protein was induced by the 1 mM IPTG essentially as described by Smith et al.,(Gene 67:31, 1988). The fusion protein was isolated by electroelution from SDS-PAGE.

PYK2— The full length cDNA sequence of PYK2 was subcloned into the following mammalian expression vectors: PLSV; downstream the SV40 early promoter, pLXSN-retroviral vector; downstream the Mo-MuLV long terminal repeat; pRK5; downstream the CMV promoter.

PYK2-HA— the influenza virus hemagglutinin peptide (YPYDVPDYAS) [SEQ ID NO 7] was fused to the C-terminal end of PYK2 utilizing the following oligonucleotide primers in the PCR: 5'-CACAATGTCTTCAAA CGCCAC-3' [SEQ ID NO 8] and 5'-GGCTCTAGATCA CGATGCGTAGTCAGGGACATCGTATGGGRACTCTG CAGGTGGGT GGGCCAG-3'. [SEQ ID NO 9] The amplified fragment was digested with RsrII and Xbal and used to substitute the corresponding fragment of PYK2. The nucleotide sequence of the final construct was confirmed by DNA sequencing.

Kinase negative mutant— in order to construct a kinase negative mutant, Lys (457) was substituted to Ala by site directed mutagenesis utilizing the 'Transformer Site-Directed Mutagenesis Kit' (Clontech). The oligonucleotide sequence was designed to create a new restriction site of Nrul. The nucleotide sequence of the mutant was confirmed by DNA sequencing. The oligonucleotide sequence that was used for mutagenesis is: 5'-CAATGTAGCTGTCGC GACCTGCAAGAAAGAC-3' [SEQ ID NO 10] (Nrul site—bold, Lys-AAC substituted to Ala-GCG underline).

Rak-HA— The rak cDNA subcloned in pBluescript was obtained from Bernardu Rudi (N.Y.U. medical center). The influenza virus hemagglutinin peptide was fused to the C-terminal end of Rak essentially as described for PYK2. The oligonucleotide primers that were used in the PCR were: 5'-GCCAGCAGGCCATGTCACTGG-3' [SEQ ID NO 11] and 5'-CGGAATTCTTACGATGCGTAGTCAGG GACATCGTATGGGTAGACATCAGTTAACAT TTTG-3'. [SEQ ID NO 12] The par product was digested with ball and EcoRI and was used to substitute the corresponding fragment at the C-terminal end of Rak. The Rak-HA CDNA was subcloned into pRK5 downstream the CMV promotor and into the retroviral vector pLXSN, downstream the Mo-MuLV long terminal repeat.

Immunoprecipitation and Immunoblot Analysis

Cells were lysed in lysis buffer containing 50 mM N-2-hydroxyethylpiperazine-N'-2-ethanesulferic acid (HEPES pH 7.5), 150 mM NaCl, 10% glycerol, 1% Triton X-100, 1.5 mM MgCl$_2$, 1 mM ethyleneglycol-bis (β-aminoethyl ether) -N,N,N'N'-tetraacetic acid (EGTA), 10 μg leupeptin per ml, 10 μg aprotinin per ml, 1 mM phenylmethylsulfonyl fluoride (PMSF), 200 μM sodium orthovanadate and 100 mM sodium fluoride. Immunoprecipitations were performed using protein A-sepharose (Pharmacia) coupled to specific antibodies. Immunoprecipitates were washed either with HNTG' solution (20 mM HEPES buffer at pH 7.5, 150 mM NaCl, 10% glycerol, 0.1% Triton X-100, 100 mM sodium fluoride, 200 μM sodium orthovanadate) or successively with H' solution (50 mM Tris-HCl pH8, 500 mM NaCl, 0.1% SDS, 0.2% Triton X-100, 100 mM NaF, 200 μM sodium orthovanadate) and L' solution (10 mM Tris-HCl pH 8, 0.1% Triton X-100, 100 mM NaF, 200 μM sodium orthovanadate).

The washed immunoprecipitates were incubated for 5 min with gel sample buffer at 100° C. and analyzed by sodium dodecyl sulfate polyacrylamide gel electrophoresis (SDS-PAGE). In some experiments the gel-embedded proteins were electrophoretically transferred onto nitrocellulose. The blot was then blocked with TBS (10 mM Tris pH 7.4, 150 mM NaCl) that contained 5%. low fat milk and 1% ovalbumin. Antisera or purified mAbs were then added in the same solution and incubation was carried out for 1 h at 22° C. For detection the filters were washed three times (5 min each wash) with TBS/0.05% Tween-20 and reacted for 45 min at room temperature with horseradish peroxidase-conjugated protein A. The enzyme was removed by washing as described above, and the filters were reacted for 1 min with a chemiluminescence reagent (ECL, Amersham) and exposed to an autoradiography film for 1–15 min.

In vitro kinase assay

This was carried out on immunoprecipitates in 50 μl HNTG (20 mM Hepes pH 7.5, 150 mM NaCl, 20% glycerol, 0.1% Triton X-100) containing 10 mM MnCl$_2$ and 5 μCi or [mN-$^{32}$P]ATP for 20 min at 22° C. The samples were washed with H', M' and, L' washing solutions, boiled for 5 min in sample buffer and separated by SDS-PAGE.

Isolation of ACK/PYK

ACK/PYK may be isolated as described in Manser et al., Nature, 363:364–367, 1993. Comparison analysis of the full length sequence of ACK/PYK with other tyrosine kinases indicates that is not closely related to any of these, although it has some similarity to the focal adhesion kinase. Therefore, ACK/PYK represents a separate class of tyrosine kinases and isolation of related genes that belong to the same class is a major accomplishment.

Example 1

Isolation of PYK-2 cDNA

To identify genes related to the ACK/PYK protein tyrosine kinase, the polymerase chain reaction (PCR) was applied in combination with degenerated oligonucleotide primers based upon conserved motifs of the kinase domain of PTKs.

Oligonucleotides primers specifically designed to a highly conserved N-terminal motif of PTKs within subdomain TK6 (IHRDLAARN) SEQ ID NO 13. and ACK/PYK specific C-terminal primers within subdomain TK9 (WMFGVTLW) SEQ ID NO 14. were utilized. The amplification reactions with cDNA templates from 8 different sources gave rise to fragments of 0.2–0.9 kb. The PCR products were subcloned into pBlueScript and screened by DNA sequencing and hybridization under low stringency conditions.

A cDNA fragment of 210 bp from rat spinal cord was identified which is highly related to the Focal Adhesion Kinase (FAK). The fragment was sequenced in the 3' and 5' directions and was subsequently used as a probe to screen cDNA libraries (human fetal brain λgt 10 and human brain λgt 11, 6×10$^5$ recombinant clones each).

Several overlapping clones spreading 1.5–3 kb were isolated and their cDNA inserts were analyzed by PCR, restriction mapping and sequencing. Two clones (#1 and #11) were chosen for further analysis and subcloning. Clone #1 contains an insert of 2.7 kb from the 5' end of the gene, and clone #11 contains an insert of 3 kb from the 3' end of the gene.

By utilizing a series of subclones and synthesized oligonucleotide primers the full length sequence of PYK-2 was determined. The sequence analysis resulted in a composite sequence of 3309 bp long which contains a 104 bp 5' untranslated region, a 3021 bp coding region and 184 bp 3' untranslated region. The ATG encoding the translation initiation codon is preceded by four translation stop codons in all reading frames.

The long open reading frame encodes a protein of 1007 amino acids (predicted molecular mass of 110,770d) whose structural organization is very similar to FAK. The PYK-2 protein contains a long N-terminal sequence of 422 amino acids followed by a tyrosine kinase catalytic domain. The PYK-2 protein also contains the structural motifs common to all PTKS, two proline rich domains (19.6% and 17% proline respectively) and a focal adhesion targeting (FAT) motif in the C-terminal end. Comparison analysis of the amino acid sequence of PYK-2 with the human FAK revealed 52% identity between the two proteins. The kinase domain and the FAT sequence are most closely related (62% homology).

The PYK-2 protein contains several predicted binding sites for intracellular substrates. For example, YLMV [SEQ ID NO 15] is a predicted binding site for GRB2 SH2 domain—tyrosine 879 of PYK-2. YVVV [SEQ ID NO 16] is a predicted binding site for SHPTP2 —tyrosine 903 of PYK-2. There are predicted phosphorylation sites for PKC, PKA and Ca/Calmodulin kinase. In addition, tyrosine 402 is a predicted autophosphorylation site of PYK-2 and it may be involved in the binding of a src SH2 domain. This is based on the homology between tyrosine 397 of FAK which was mapped as a major autophosphorylation site both in vivo and in vitro. This tyrosine provides an high affinity binding site for a src SH2 domain. Both tyrosine 397 of FAK and tyrosine 402 of PYK-2 are located at the juncture of the N-terminal and the catalytic domain and are followed by sequence (Y)AEI which is very similar to the consensus of the high affinity src SH2 domain binding peptide YEEI.

Example 2

Antibodies to PYK-2

Antibodies against PYK-2 were raised in rabbits immunized either with GST fusion protein containing residues of PYK-2 or with synthetic peptide corresponding to the 15 amino acids at the N-terminal end of PYK-2. The antibodies are specific to PYK-2 and they do not cross react with FAK.

Example 3

Pattern of PYK-2 Expression

The tissue distribution of PYK-2 expression was determined by Northern blot analysis. Poly(A)$^+$ RNAs were purified from mouse tissues (liver, lung, spleen, kidney, heart, brain, skin, uterus) and hybridized with two different probes corresponding to two different regions of the PYK-2 gene. The results were identical in both cases. A 4.2 kb PYK-2 transcript is relatively abundant in the brain but was also found in lower levels in the spleen and in the kidney.

The expression of PYK-2 in different cell lines was analyzed by IP/IB utilizing anti-PYK-2 antibodies directed to the kinase domain as described previously (GST-PYK-2). The expression pattern is summarized in table 1. Some of the interesting observations are a mobility shift of PYK-2 after differentiation of CHRF and L8057 (premegakaryocyte cell lines) by TPA, high expression of Fak and PYK-2 in different cell lines; and in XC cells (rat sarcoma) PYK-2 is phosphorylated on tyrosine.

Example 4
Properties of PYK-2 protein

In order to analyze the biochemical properties of PYK-2 the full length cDNA was subcloned into the two mammalian expression vectors RK5 and pLSV. In parallel, an expression vector encoding the PYK-2 protein fused to the influenza virus hemagglutinin peptide was constructed. This construct was used to identify the protein utilizing anti-HA antibodies.

Example 5
Transient transfection pLSV-PYK-2-HA was transfected into cos cells. The protein was expressed at the predicted molecular mass (~116 kD) as determined by IP and IB with anti-HA antibodies. The protein is an active kinase as determined by in vitro kinase assay utilizing ($\lambda^{32}$P) ATP or an in vitro kinase assay utilizing cold ATP and immunoblotting with anti-phosphotyrosine antibodies.

Example 6
Stable cell lines

The PYK-2 cDNA cloned in pLSV was cotransfected with pSV2neo into PC12 cells and NIH3T3 in order to establish stable cell lines. G418 resistant colonies were screened by immunoprecipitating and immunoblotting.

NIH3T3 cell lines were established that overexpress the PYK-2 and the PYK-2-HA protein. In these cells PYK-2 undergoes tyrosine phosphorylation in response to PDGF, EGF and aFGF. The level of phosphorylation is not so high. The stronger effect is achieved by TPA treatment (6 $\mu$M) after 15 min incubation at 37° C. as determined by time course analysis.

Example 7
PC12 cells

The phosphorylation of PYK-2 on tyrosine residue in response to different stimuli was analyzed by immunoprecipitation of PYK-2 and immunoblotting with anti-phosphotyrosine antibodies and vice versa.

The following treatment were used: Bradykinin, TPA, forskolin, forskolin+TPA, bradykinin+forskolin, NGF, Neuropeptide Y. Cholera toxin, Cholera toxin+TPA, Cholera toxin+bradykinin, pertusis toxin, pertusis toxin+TPA, bradykinin+pertusis toxin, calcium ionophore A23187, bombesin.

The following results were obtained: PYK-2 undergoes tyrosine phosphorylation in response to TPA (1.6 $\mu$M 15 min at 37° C.), bradykinin (1 $\mu$M 1 min at 37° C.) and calcium ionophore A23187 (2 $\mu$M 15 min at 37° C.). Forskolin increase the response of TPA but does not give any signal by itself. Cholera toxin gave higher signal in combination with TPA and bradykinin but didn't cause phosphorylation of PYK-2 alone. Pertusis toxin also induced the response of TPA and bradykinin but didn't cause any response alone. In order to determined if the bradykinin effect is mediated by PKC signaling pathway, attempts to down regulate PKC by chronic treatment with TPA (twice) did not give a clear answer.

One interpretation of these results is that PKC and PKA (and maybe Ca/calmudolin kinase) induce the autophosphorylation of PYK-2 in response to ser/the phosphorylation. This interpretation may be checked by utilizing specific inhibitors to PKC and PKA and by phosphamino-acid analysis.

Example 8
Phosphorylation of RAK 293 cells in 65 mm plates were transiently transfected either with the potassium channel-RAK-HA alone, or together with Fak, PYK2 or the PYK2-kinase negative mutant (PKN). 12 hr following transfection the cells were grown in DMEM containing 0.3% fetal bovine serum for 24 hours. The cells were either stimulated with PMA (1.6 $\mu$M) or with calcium ionophore A23187 (6 $\mu$M) for 15 min at 37° C. or left unstimulated. The cells were solubilized and the expression level of each protein was determined by western blot analysis. The Rak protein was immunoprecipitated by anti-HA antibodies and its phosphorylation on tyrosine residues was analyzed by western blot analysis utilizing anti-phosphotyrosine antibodies following immunoprecipitation of the proteins either with anti-PYK2 antibodies (for PYK2 and PKN) or with anti Fax antibodies for (Fak).

The expression level of each protein (Rak PYK2, PKN and Fak) and the tyrosine phosphorylation of Rak, PYK2, PKN and Fak were measured.

Only the kinase active PYK2 protein phosphorylated the potassium channel. No phosphorylation was observed with kinase negative PYK2 or with FAK.

Other embodiments are within the following claims.

---

What is claimed is:

1. An isolated or purified nucleic acid molecule encoding a polypeptide comprising the amino acid sequence of SEQ ID NO:1.

2. The nucleic acid molecule of claim 1, wherein said nucleic acid molecule is isolated.

3. An isolated or purified nucleic acid molecule comprising at least one hundred and five nucleotides of said molecule of claim 1.

4. The nucleic acid molecule of claim 3, wherein said nucleic acid molecule is present in a sample at least from 10% to 20% more frequently than any other nucleotide sequence.

5. The nucleic acid molecule of claim 1, wherein said nucleic acid molecule is purified.

6. The nucleic acid molecule of claim 5, wherein said nucleic acid molecule is at least two times more pure on a mg/ml basis than in its natural environment.

7. The nucleic acid molecule of claim 6, wherein said nucleic acid molecule is at least five times more pure on a mg/ml basis than in its natural environment.

8. The nucleic acid molecule of claim 1, wherein said nucleic acid molecule encodes a polypeptide consisting of the amino acid sequence of SEQ ID NO:1.

9. The nucleic acid molecule of claim 1, said nucleic acid molecule comprising the nucleotide sequence of SEQ ID NO:2.

10. A recombinantly made nucleic acid molecule encoding a polypeptide comprising the amino acid sequence of SEQ ID NO:1, said nucleic acid molecule operably linked to a regulatory sequence to allow expression of said nucleic acid molecule.

11. The nucleic acid molecule of claim 10, wherein said nucleic acid molecule encodes a polypeptide consisting of the amino acid sequence of SEQ ID NO:1.

12. The nucleic acid molecule of claim 10, said nucleic acid molecule comprising the nucleotide sequence of SEQ ID NO:2.

13. The nucleic acid molecule of claim 12, said nucleic acid molecule consisting of the nucleotide sequence of SEQ ID NO:2.

14. A genetically engineered host cell containing a nucleotide sequence encoding a polypeptide comprising the amino acid sequence of SEQ ID NO:1, said nucleotide sequence operably linked to a regulatory sequence to allow expression of said nucleotide sequence.

15. The host cell of claim 14, wherein said nucleic acid molecule encodes a polypeptide consisting of the amino acid sequence of SEQ ID NO:1.

16. The host cell of claim 14, wherein said nucleic acid molecule comprises the nucleotide sequence of SEQ ID NO:2.

17. The host cell of claim 16, wherein said nucleic acid molecule consists of the nucleotide sequence of SEQ ID NO:2.

18. The host cell of claim 14, wherein said host cell is prokaryotic.

19. The host cell of claim 14, wherein said host cell is eukaryotic.

20. An isolated, purified, or recombinantly made nucleic acid molecule comprising at least one hundred and five nucleotides of the nucleic acid sequence of SEQ ID NO:2, said nucleic acid molecule encoding a polypeptide possessing at least one of the functional activities of the amino acid sequence of SEQ ID NO:1, wherein said actives are phosphorylation and regulation of potassium channels.

21. An expression construct containing the nucleic acid molecule of claim 20.

22. A genetically engineered host cell containing the nucleotide sequence of claim 20, said nucleotide sequence operably linked to a regulatory sequence to allow expression of said nucleotide sequence.

23. The host cell of claim 22, wherein said host cell is prokaryotic.

24. The host cell of claim 22, wherein said host cell is eukaryotic.

25. The nucleic acid molecule of claim 9, said nucleic acid molecule consisting of the nucleotide sequence of SEQ ID NO:2.

* * * * *